US012023410B2

United States Patent
Widgerow et al.

(10) Patent No.: US 12,023,410 B2
(45) Date of Patent: Jul. 2, 2024

(54) MICRO/NANOBUBBLE SOLUTIONS FOR TISSUE PRESERVATION AND GENERATION THEREOF

(71) Applicant: THE REGENTS OF THE UNIVERSITY OF CALIFORNIA, Oakland, CA (US)

(72) Inventors: Alan D. Widgerow, Irvine, CA (US); Derek Banyard, Orange, CA (US); Michael Klopfer, Oakland, CA (US); Lohrasb H. Sayadi, Orange, CA (US)

(73) Assignee: The Regents of the University of California, Oakland, CA (US)

( * ) Notice: Subject to any disclaimer, the term of this patent is extended or adjusted under 35 U.S.C. 154(b) by 787 days.

(21) Appl. No.: 16/615,483

(22) PCT Filed: May 22, 2018

(86) PCT No.: PCT/US2018/033834
§ 371 (c)(1),
(2) Date: Nov. 21, 2019

(87) PCT Pub. No.: WO2018/217710
PCT Pub. Date: Nov. 29, 2018

(65) Prior Publication Data
US 2020/0197318 A1 Jun. 25, 2020

Related U.S. Application Data

(60) Provisional application No. 62/509,294, filed on May 22, 2017.

(51) Int. Cl.
*A61K 9/51* (2006.01)
*A61K 9/08* (2006.01)
(Continued)

(52) U.S. Cl.
CPC .................. *A61K 9/51* (2013.01); *A61K 9/08* (2013.01); *A61K 9/5089* (2013.01); *A61M 1/85* (2021.05);
(Continued)

(58) Field of Classification Search
CPC ........ A61M 1/85; A61M 1/94; A61M 3/0279; A61M 3/0283; A61M 35/30; A61M 1/77
See application file for complete search history.

(56) References Cited

U.S. PATENT DOCUMENTS 9,402,803 B2 8/2016 Archambeau
10,195,632 B1 * 2/2019 Baumgartner .......... A61L 9/032
(Continued)

FOREIGN PATENT DOCUMENTS

WO 2016169416 10/2016

OTHER PUBLICATIONS

Banyard et al., AAPS and PSRC Abstract Supplement, 2016, p. 49.
(Continued)

*Primary Examiner* — Kai H Weng
*Assistant Examiner* — Nhu Q. Tran
(74) *Attorney, Agent, or Firm* — Riverside Law LLP

(57) ABSTRACT

The invention provides an apparatus for the generation and administration of a micro-nanobubble solution to a tissue, a method for the treatment of a tissue with a solution of micro-nanobubbles, and a kit for the treatment of tissue with micro-nanobubbles.

12 Claims, 22 Drawing Sheets

(51) Int. Cl.
*A61K 9/50* (2006.01)
*A61M 1/00* (2006.01)
*A61M 3/02* (2006.01)
*A61M 35/00* (2006.01)

(52) U.S. Cl.
CPC ........ *A61M 3/0279* (2013.01); *A61M 3/0283* (2013.01); *A61M 35/30* (2019.05); *A61B 2218/001* (2013.01); *A61M 1/77* (2021.05); *A61M 1/94* (2021.05); *A61M 2205/3344* (2013.01)

(56) References Cited

U.S. PATENT DOCUMENTS

| | | | |
|---|---|---|---|
| 2009/0051055 A1* | 2/2009 | Park | B01F 23/234 |
| | | | 261/115 |
| 2012/0078140 A1 | 3/2012 | Nita | |
| 2013/0085462 A1* | 4/2013 | Nip | A61M 1/90 |
| | | | 604/315 |
| 2014/0148687 A1 | 5/2014 | Keenan | |
| 2014/0158631 A1* | 6/2014 | Govind | B01D 17/0205 |
| | | | 252/60 |
| 2014/0255454 A1* | 9/2014 | Archambeau | B29D 11/00096 |
| | | | 424/613 |
| 2016/0325028 A1* | 11/2016 | Locke | A61M 1/92 |
| 2018/0099008 A1* | 4/2018 | Kang | A61P 9/10 |
| 2018/0369462 A1* | 12/2018 | Anderson | A61M 1/964 |
| 2019/0298653 A1* | 10/2019 | Yamanouchi | A61K 9/08 |

OTHER PUBLICATIONS

Bez et al., Sci. Transl. Med., 2017, vol. 9, Issue 390, eaal3128 (9 pages).

Klopfer et al., "Micro and Nanobubbles for Wound Healing Applications," Dissertation Submitted in Partial Satisfaction of the Requirements for the Degree of Doctor of Philosophy in Biomedical Engineering, 2015 (68 pages).

* cited by examiner

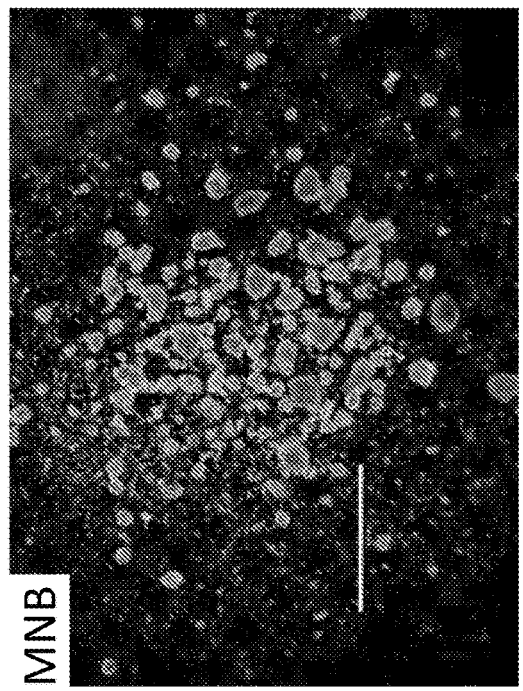
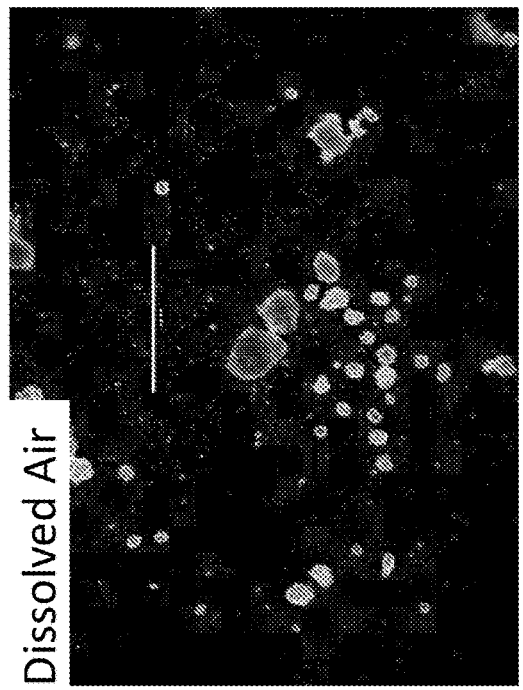
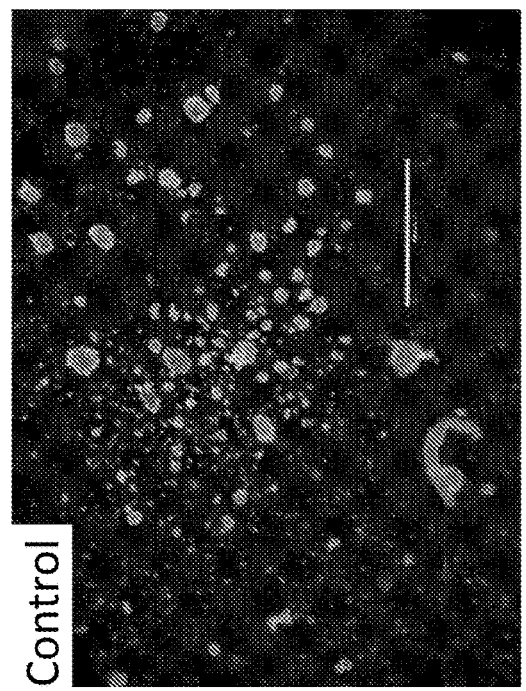
Figure 22

MICRO/NANOBUBBLE SOLUTIONS FOR TISSUE PRESERVATION AND GENERATION THEREOF

CROSS-REFERENCE TO RELATED APPLICATIONS

The present application is a 35 U.S.C. § 371 national phase application from, and claiming priority to, International Application No. PCT/US2018/033834, filed May 22, 2018, which claims priority under 35 U.S.C. § 119(e) to U.S. Provisional Patent Application Ser. No. 62/509,294, filed May 22, 2017, all of which are incorporated herein by reference in their entireties.

BACKGROUND OF THE INVENTION

Micro-nanobubbles (MNBs) offer a new technology for creating oxygen-enriched fluids. Bubbles are gas-containing cavities in an aqueous solution. Microbubbles have a diameter between 1 and 100 μm, and nanobubbles less than 1 μm. Fluids can be saturated with various gases, e.g. oxygen, using MNB technology, and such fluids are an excellent vehicle for external oxygen delivery to tissues. Nanobubbles have several unique properties (Ushikubo et al. Colloids and Surfaces A: Physiochem Eng Aspects 2010, 361:31-37; Demangeat Homeopathy 2015; 104: 101-115). They can form freely and remain in an aqueous solution for extended periods of time with the capacity to act as a reservoir and store oxygen; thus, interest in micro-nanobubbles is growing (Klopfer, Micro and Nanobubbles for Wound Healing Applications: University of California, Irvine, 2015; Tsuge, Micro- and Nanobubbles: Fundamentals and Applications. Singapore: Pan Stanford Publishing; 2014). Currently, applications for solutions containing MNBs are found in multiple industries (Burns, et al., Sep Purif Technol 1997; 11(3): 221-232; Li and Tsuge, J Chem Eng Jpn 2006; 39(8): 896-903; Li P and Tsuge, J Chem Eng Jpn 2006; 39(11): 1213-1220; Yin, et al., Int J Nanomedicine 2012; 7: 895-904). They have been utilized in medicine as contrast agents for ultrasonography and drug delivery vehicles (Paefgen, et al., Front Pharmacol 2015; 6: 197). Efficient gas transfer and cleaning are the most noted applications. That noted, MNB solutions for medical applications remain to be explored.

Dissolved gas in microbubble solution can break up surface films via localized bi-phasic (water/air) interaction. Free floating microbubbles can clear solutions of particulates through nucleation and flocculation mechanisms.

Oxygenation is important in reducing infection. The levels of oxygen that are required to reduce infection (partial pressure of 80-300 mmHg) are beyond those encountered in room air diffusing across a fluid layer (Klopfer, Micro and Nanobubbles for Wound Healing Applications: University of California, Irvine; 2015). This is mainly because, at standard atmospheric pressure, oxygen creates an oxygen partial pressure of 760 mmHg as opposed to room air (at 21% $O_2$), which has an oxygen partial pressure of 160 mmHg. Therefore, supplemental oxygen is necessary to reduce infection by inducing an acute increase in reactive oxygen species (ROS) levels in wound neutrophils and macrophages (Allen, et al., Arch Surg 1997; 132(9): 991-996). Inactivity of these cell types can severely affect the body's ability to combat bacterial loads in wounds. Numerous growth factors (e.g., PDGF, TGF-β) rely on ROS for their functionality (Sundaresan, et al., Science 1995; 270 (5234): 296-299).

Chronic non-healing wounds constitute a major health problem particularly in the elderly population. Local tissue hypoxia, related to health problems such as diabetes, venous stasis and peripheral vascular disease, is a common feature accompanying all types of chronic wounds with ischemia reperfusion cycles contributing significantly to tissue damage (Widgerow, WOUNDS 2012; 24(3): 58-66). Oxygen delivery has been identified as a major factor affecting wound healing, and it is accepted that limited oxygenation leads to a chronic nonhealing ulcer (Winfeld, WOUNDS 2014; 26(5): E39-E47; Gulino, et al., Mediators Inflamm 2015; 2015: 964838). Maintaining an appropriate level of oxygen in these wounds continues to be a challenge (Winfeld, WOUNDS 2014; 26(5): E39-E47).

The mean subcutaneous partial oxygen ($pO_2$) levels in normal skin at a depth of 3-4 mm are in the range of 45-53 mmHg (Whitney, et al., Biol Res Nurs 2001; 2(3): 206-215), but research suggests that improving $pO_2$ to 54-65 mmHg would significantly improve wound healing in difficult to treat wounds (Asmis, et al., Int Would J 2010; 7(5): 349-357). Oxygen has been reported to increase fibroblast migration and proliferation (Knighton, et al., Surgery 1981; 90(2): 262-270), increase collagen production and tensile strength (Hunt, J Trauma 1990; 30(12 Suppl): S122-S128), stimulate angiogenesis (Knighton, et al., Surgery 1981; 90(2): 262-270), and promote macrophage chemotaxis (Bosco, et al., J Rheumatol 2009; 36(6): 1318-1329). The majority of oxygen in the bulk of the skin is supplied internally via the vasculature. Cellular metabolic demands and low bulk diffusivity limit the depth of external oxygen to tissue. For a wound, an increase in metabolism in a condition of damage to the normal vasculature based oxygen transfer can rapidly lead to low oxygen concentrations at a wound site. The central regions of a chronic wound may have $pO_2$ levels as low as 0-5 mmHg. At levels below 20 mmHg, cells switch from aerobic metabolism to anaerobic metabolism with lactate production, and the resulting reduced pH can inhibit healing (Asmis, et al., Int Would J 2010; 7(5): 349-357; LaVan and Hunt, Clin Plast Surg 1990; 17(3): 463-472; Hess, et al., Annals of plastic surgery 2003; 51(2): 210-218; Hunt, J Trauma 1990; 30(12 Suppl): S122-S128). Preliminary simulation and in vivo studies have shown that micro-nanobubbles can increase the measurable oxygen tension of a skin model through external application (Klopfer, Micro and Nanobubbles for Wound Healing Applications: University of California, Irvine; 2015).

In the context of wound care, an apparatus that functions as a negative pressure wound therapy (NPWT) system, which involves the controlled application of subatmospheric pressure to the wound environment and simultaneously producing MNBs for delivery of an oxygenated solution to irrigate the wound, provides a major new option for wound therapy. The novel combination of negative pressure inducing delivery of oxygenated fluids creates a new paradigm of wound microdeformation and granulation induction together with tissue oxygenation. In one embodiment, rounds of negative pressure and MNB irrigation are alternating. In another embodiment, MNB irrigation and negative pressure application are simultaneous, creating a continuous flow of a MNB solution over the tissue. The NPWT treatment comprises alternating periods of negative pressure and MNB solution rinse.

Micro-nanobubbles which can serve as a vehicle for topical oxygen therapy (TOT) are a potential advance in the treatment of non-healing ulcers (Tawfick and Sultan, Vasc Endovascular Surg 2013; 47(1): 30-37; Prato, et al., PLoS One 2015; 10(3): e0119769). Topical oxygen therapy allows direct oxygen uptake by the injured tissue via an external delivery route. TOT delivery systems are inexpensive, simple to use, and do not pose the systemic risks seen with full-body hyperbaric oxygen systems (Sano and Ichioka, Wounds International 2015; 6(1): 20-26). The same physical methods of delivery to bodily tissues holds for cells and tissues in culture (Klopfer, Micro and Nanobubbles for Wound Healing Applications: University of California, Irvine; 2015). In addition, in the field of transplantation, tissue hypoxia is a significant factor limiting organ preservation times and cell survival prior to transplantation. As such micro-nanobubbles can act as an agent for organ/tissue oxygenation after harvest from the donor.

There is a continuing need in the art for methods of supplying oxygen to tissues as well as for devices capable of generating micro-nanobubbles. The present invention addresses this continuing need in the art.

SUMMARY OF INVENTION

An apparatus for the administration of micro-nanobubbles to a tissue or wounds is described. The apparatus includes a liquid source, a gas source, a micro-nanobubble generation pump (examples of this type of pump include but are not exclusive to lobular pumps, gear pumps, gerotor, and turbine pumps) connected to and downstream of the liquid source and the gas source, a decompression nozzle downstream of the pressure chamber/pump, and a treatment applicator downstream of the decompression nozzle. The treatment applicator can have at least one outlet connected to a vacuum source and the decompression nozzle is suitable for generating micro-nanobubbles within the solution. In one embodiment, the apparatus comprises a compression chamber. In one embodiment, the micro-nanobubble generation pump imparts shear on the pumped fluid during compression. In one embodiment, the vacuum source is a negative pressure vacuum source. In one embodiment, the apparatus includes a collection chamber between the vacuum source and the treatment applicator. In one embodiment, the apparatus includes an air pump downstream of the decompression nozzle. In one embodiment, the apparatus includes air injection and the application of pneumatic pressure on fluid upstream of the decompression nozzle. In one embodiment, the apparatus includes at least one pressure sensor downstream of the air pump and upstream of the treatment applicator. In one embodiment, the apparatus includes air injection and the application of pneumatic pressure on fluid in a pressurization chamber downstream of the decompression nozzle. In one embodiment, the apparatus includes at least one pressure sensor downstream of the pressurization chamber and upstream of the treatment applicator. In one embodiment of the invention, the treatment applicator is a hydrosurgery system or lavage application wand. In another embodiment, the treatment applicator is an air-tight dressing. In another embodiment, the treatment applicator is an air-permeable dressing. In one embodiment, the treatment applicator is an occlusive dressing. In one embodiment, the treatment applicator is a saturated dressing. In another embodiment, the treatment applicator is a saturated dressing exposed to room air. In another embodiment, the treatment applicator is a vessel with an inlet and an outlet.

In one embodiment, the gas source is an oxygen tank. In another embodiment, the gas source is an ozone generator. In one embodiment, the gas source is ambient air. In another embodiment, the treatment applicator incorporates the decompression nozzle. In another embodiment, generation is monitored by one or more sensors and used to maintain generation in a feedback servomechanism configuration affecting generation flow, pressure, and nozzle configuration to maintain consistent micro-nanobubble generation parameters and consistent output.

Also described is a method for the treatment of a tissue with a solution of micro-nanobubbles. The method includes the steps of providing a flow of liquid from a liquid source, introducing a gas from a gas source into the flow of liquid to create a gas/liquid mixture, passing the gas/liquid mixture through a micro-nanobubble generation pump, passing the gas/liquid mixture through decompression nozzle to generate micro-nanobubbles in the gas/liquid mixture, introducing the gas/liquid mixture having the micro-nanobubbles into a treatment applicator, and contacting a target tissue with the micro-nanobubbles via the treatment applicator. In one embodiment, the method also includes the step of applying a negative pressure at the treatment applicator. In another embodiment, the method includes the step of pressuring the gas/liquid mixture having the micro-nanobubbles. In one embodiment, applying the negative pressure at the treatment applicator and contacting the target tissue with the micro-nanobubbles via the treatment applicator occurs simultaneously. In another embodiment, applying the negative pressure at the treatment applicator occurs after contacting the target tissue with the micro-nanobubbles via the treatment applicator. In one embodiment, the tissue comprises a wound. In one embodiment, the tissue comprises a wound covered with wound dressing(s). In one embodiment, the tissue comprises a wound covered with dressing and negative pressure. In one embodiment, the tissue comprises allograft tissue. In another embodiment, the tissue comprises autograft tissue. In another embodiment, the tissue comprises ex-vivo tissue including tissues and samples or cultures of lipoaspirate or islet cells. In one embodiment, the liquid comprises physiologic clinical solutions (e.g. water, normal saline, half-normal saline, ringers lactate, D5W, transplant preservation solutions). In another embodiment, the liquid comprises at least one antimicrobial agent.

Also described is a kit for the treatment of a tissue with a solution of micro-nanobubbles. The kit includes an apparatus for the administration of micro-nanobubbles to a tissue and an instructional material. In one embodiment, the kit comprises sterile consumable components for the generation, delivery, and administration of a solution of MNBs. In one embodiment, the kit comprises sterilizable durable components for the generation, delivery, and administration of MNBs. In one embodiment, the kit comprises both sterile consumable components and sterilizable durable components.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 5A and 5B, depicts zeta potential measurements of MNBs generated with two different methods. FIG. 5A is a plot of zeta potential for DGD-treated deionized water. FIG. 5B is a plot of zeta potential for AMF-treated deionized water.

FIG. 22 is a series of photographs of pancreatic islet cells grown in control media, media with dissolved air, and media treated with a micro-nanobubble solution.

DETAILED DESCRIPTION

Figure 1:
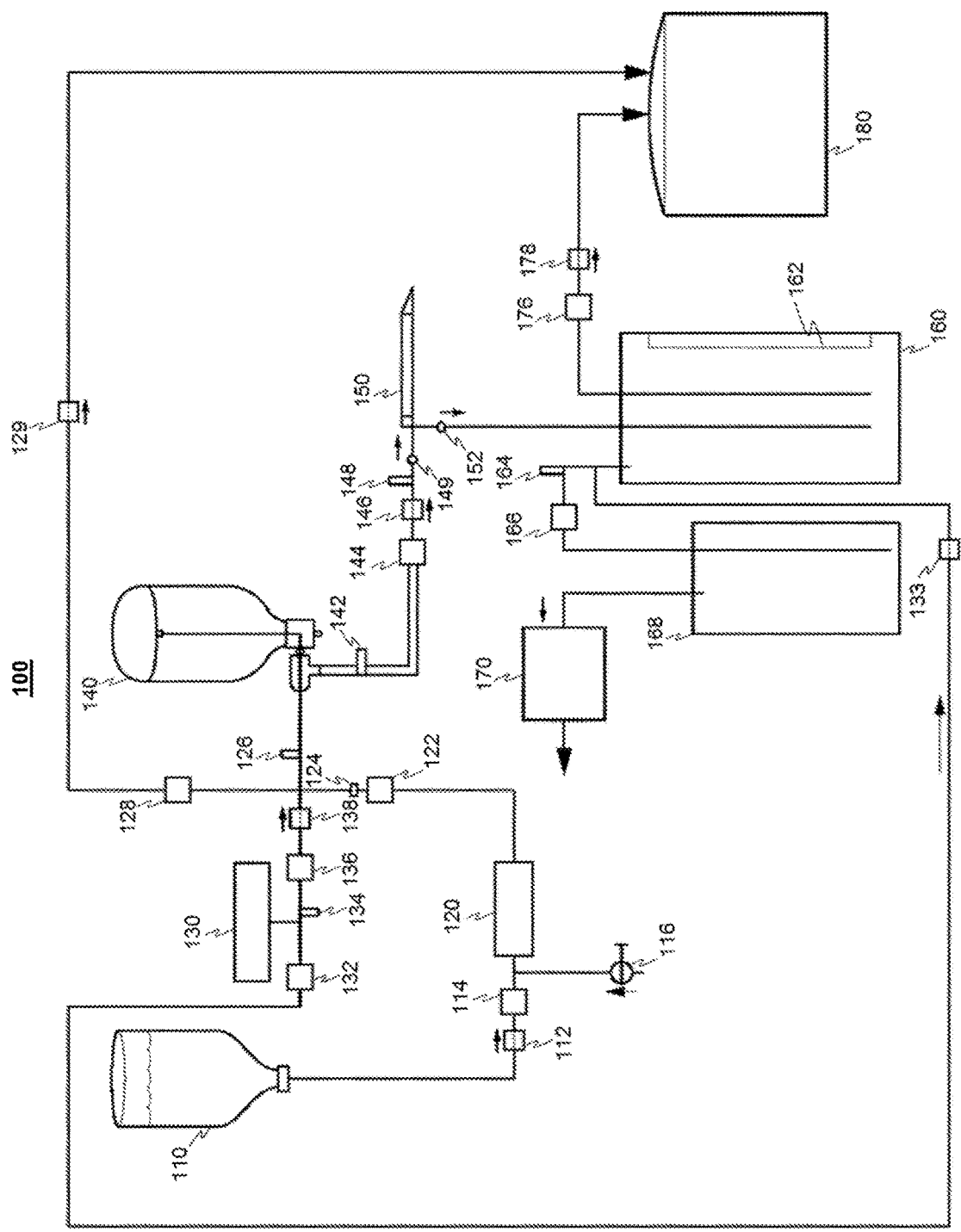
FIG. 1 is a block diagram of an exemplary MNB generation apparatus.

It is to be understood that the figures and descriptions of the present invention have been simplified to illustrate elements that are relevant for a clear understanding of the present invention, while eliminating, for the purpose of clarity, many other elements found in the art related to MNB generation and the use thereof. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods, materials and components similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, "wound exudate", or, simply, "exudate", generally refers to any fluid output from a wound, e.g., blood, serum, and/or pus, etc. As used herein, "fluid" generally refers to a liquid, a gas or both.

"Graft" refers to a cell, tissue, organ or otherwise any biological compatible substrate for transplantation.

"About" as used herein when referring to a measurable value such as an amount, a temporal duration, and the like, is meant to encompass variations of ±20%, ±10%, ±5%, ±1%, or ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Description

Chronic non-healing wounds constitute a major health problem particularly in the elderly population. Local tissue hypoxia, related to health problems, such as diabetes, venous stasis and peripheral vascular disease, is a common feature accompanying all types of chronic wounds with ischemia reperfusion cycles contributing significantly to tissue damage. Oxygen delivery has been identified is a major factor affecting wound healing, and it is accepted that limited oxygenation leads to a chronic nonhealing ulcer. Maintaining an appropriate level of oxygen in these wounds continues to be a challenge.

In one aspect, the present invention relates to a method of treatment of a tissue with a solution of micro-nanobubbles. According to the current invention, the tissues are contacted with a liquid comprising micro-nanobubbles such that the contents of the bubbles are released to the surface of the tissue or within the tissue. The method can optionally include the use of negative pressure wound therapy (NPWT). The use of MNB oxygenated solutions for instillation combined with NPWT significantly aids in the healing of soft tissue injuries, especially when the healing process is impaired due to diabetes. Due to their stability, MNBs are used as agents to transport oxygen to hypoxic tissue; the use of a MNB oxygenated solution for instillation combined with NPWT significantly aids in the healing of chronic ulcerating wounds.

Apparatuses of the Invention

In one aspect, the present invention relates to an apparatus for the administration of a micro-nanobubbles to a tissue or wound. An exemplary apparatus 100, such as that shown in FIG. 1, may include liquid source 110, gas inlet 116, a micro-nanobubble generation pump 120, MNB decompression nozzle 124, air pump 130, pressure chamber 140, treatment applicator 150 (connected via connectors 149 and 152), collection chambers 160 and 168, vacuum source 170, and waste container 180. Flow can be controlled via independent operation of solenoid valves 114, 122, 128, 132, 136, 144, 166, and 176, and flow direction can be controlled via check valves 112, 129, 133, 138, 146, and 178. Pressure levels can be determined via sensors 126, 134, 142, 148, and 164. In one embodiment of the invention, exemplary apparatus 100 is controlled using a control system such as exemplary control system 200, shown in FIG. 2, which includes microcontroller board 210 and computer system 225 that communicate via board input 220 and computer output 224. Control system 200 also connects to level sensor 162, status panel 290, at-a-glance indicators 280, sounding system 270, push buttons 260, switch 250, input 240, relay board 230, and pressure sensors 126, 134, 142, 148, and 164 (FIG. 1). Relay board 230 controls pumps 130 and 170 in addition to solenoid valves 114, 122, 128, 132, 136, 144, 166, and 176.

Referring to FIG. 1, an exemplary apparatus 100 may include a liquid source 110. The liquid source provides a liquid to the apparatus. In one embodiment, the liquid source comprises a physiologic clinical solution. Exemplary physiologic clinical solutions include, but are not limited to, water, normal saline, half-normal saline, ringers lactate, D5W, and transplant preservation solutions. In one embodiment, the liquid source comprises a drip bag. In one embodiment, the liquid source comprises a pump which may provide the liquid at a particular pressure. Exemplary pumps include, but are not limited to, centrifugal pumps, ANSI process pumps, axial flow pumps, booster pumps, canned motor pumps, circulator pumps, drum pumps, end suction pumps, horizontal split case pumps, jet pumps, magnetic drive pumps, multistage pumps, regenerative turbine pumps, self-priming pumps, submersible pumps, vertical sump pumps, vertical turbine pumps, well pumps, positive displacement pumps, AODD pumps, diaphragm pumps, flexible impeller pumps, gear pumps, lobe pumps, metering pumps, peristaltic pumps (hose pumps), piston pumps, plunger pumps, progressive cavity pumps, screw pumps, and vane pumps. In some embodiments, the liquid source comprises a vessel containing a liquid. In one embodiment, the vessel can be easily connected and removed depending on the desired use of the apparatus. In one embodiment, output liquid can be recirculated in use. In another embodiment the liquid can be supplied via a recirculation system relying on filtration as part of the intake. In another embodiment the liquid can be supplied via a cartridge or continuous feed system. In one embodiment active sterilization of input fluid is used including filtration on the input consisting of a filter. In one embodiment active sterilization of output fluid is accomplished with filtration or UV sterilization. In one embodiment active sterilization of output fluid is accomplished with the use of glass or quartz flow tubed and a UV germicidal source.

Gas is supplied to the MNB-generating apparatus via gas inlet 116 connected to a gas source. Examples of suitable gases include helium, nitrogen, carbon dioxide, carbon monoxide, hydrocarbons, fluorocarbons, hydrofluorocarbons, chlorofluorocarbons, oxygen, ozone, and combinations thereof. In one embodiment, the gas comprises oxygen. In another embodiment, the gas comprises ozone. In one embodiment the gas comprises ambient air. In one embodiment, the gas source comprises a chemical, electrolytic, or discharge-based gas generator. In one embodiment, the gas source comprises a gas tank. In one embodiment, the gas source comprises an oxygen tank. In one embodiment, the gas source comprises an oxygen concentration system. In another embodiment, the gas source comprises an ozone generator. In one embodiment, the gas source is easily connected to, and disconnected from, apparatus 100.

In some embodiments of the invention, inlet 116 comprises a valve to control the flow of gas to the system. Those of ordinary skill in the art will appreciate that the type of valve used is dependent on the gas used and the gas flow rate desired. In one embodiment, inlet 116 provides metered flow of gas to the system. In one embodiment, inlet 116 comprises a nozzle to cause breakup of the gas into the fluid flow stream. In one embodiment, the flow of gas to the apparatus is controlled by control system 200. In one embodiment, inlet 116 comprises a needle valve. In one embodiment, inlet 116 comprises a mixing "T"-style connector interface which permits breakup of the gas in the fluid stream due to sheer force of the moving fluid. In one embodiment, the gas flow rate is controlled manually. In other embodiments, the gas flow rate is controlled electronically via control system 200. In one embodiment, the gas flow rate is held constant throughout operation of the apparatus. In another embodiment, the gas flow rate is varied over the course of treatment with the apparatus.

Micro-nanobubble generation pump 120 generates an initial solution of microbubbles. In one embodiment, apparatus 100 comprises a compression chamber and the micro-nanobubble generation pump imparts shear on the pumped fluid during compression. Exemplary micro-nanobubble generation pumps include, but are not limited to, gear pumps, lobular pumps, gerotor pumps, and turbine pumps. In one embodiment, the micro-nanobubble generation pump 120 comprises a low-power, low-cost device such as a TOPSFLO TG-7, TOPSFLO ZC-520, or SHURFLO 2208-554, TCS MGD1000 gear pump type units. In one embodiment, the gear pump employs a lobular-type configuration. In another embodiment, the gear pump employs a vane-type configuration.

Decompression nozzle 124 converts the microbubble solution produced by micro-nanobubble generation pump 120 and pressure tank 140 into micro-nanobubbles. In one embodiment, the nozzle comprises an orifice (hole) in a sterile plastic fitting. In one embodiment, the sterile plastic comprises acrylonitrile butadiene styrene (ABS). In one embodiment, the inner diameter of the nozzle is between about 1 μm and about 1000 μm. In one embodiment, the inner diameter of the nozzle is between about 250 μm and about 1000 μm. In one embodiment, the inner diameter of the nozzle is between about 500 μm and about 1000 μm. In one embodiment, the inner diameter of the nozzle is between about 500 μm and about 750 μm. In one embodiment, the nozzle has an inner diameter of about 500 μm. In one embodiment, the nozzle has an inner diameter of about 550 μm. In one embodiment, the nozzle has an inner diameter of about 600 μm. In one embodiment, the nozzle has an inner diameter of about 650 μm. In one embodiment, the nozzle has an inner diameter of about 700 μm. In one embodiment, the nozzle has an inner diameter of about 750 μm. In one embodiment, the nozzle has an inner diameter of about 800 μm. In one embodiment, the nozzle has an inner diameter of about 850 μm. In one embodiment, the nozzle has an inner diameter of about 900 μm. In one embodiment, the decompression nozzle utilizes vortex flow. In one embodiment, the decompression nozzle utilizes multiple state decompression. In some embodiments, a plurality of decompression nozzles is used. In one embodiment, multiple decompression nozzles are used in serial. In one embodiment, multiple decompression nozzles are distributed throughout the apparatus. In one embodiment localized heating or cooling is applied to the decompression nozzle. In one embodiment localized auditory or mechanical energy is applied to the decompression nozzle. In one embodiment localized electric or magnetic fields are applied to the decompression nozzle. In one embodiment, the decompression nozzle is downstream from a compression chamber. In one embodiment, the apparatus includes air injection and the application of pneumatic pressure on fluid upstream of the decompression nozzle.

Air pump 130 and pressure chamber 140 pressurize the MNB solution generated via passage through decompression nozzle 124. Exemplary air pumps include, but are not limited to, reciprocating pumps, centrifugal/blower pumps, continuous pumps, peristaltic pumps, diaphragmatic pumps, or any other suitable mechanisms for increasing pressure known by those in the art. In some embodiments, pressure chamber 140 includes internal structures such as fins, dampers, or microstructures to modify fluid flow within the chamber. In one embodiment, ultrasonic energy is applied within or externally to chamber 140 to improve micro-nanobubble dissolution. In one embodiment, chamber 140 comprises multiple orifices or sintered metal/ceramic outlets. In one embodiment, the outlet of chamber 140 comprises decompression nozzle 124. In one embodiment, the solution enters pressure chamber 140 via high pressure spray to create a fluid vortex or a descending layer of solution against the vessel walls. In one embodiment, the solution is pressurized to between about 10 PSI and about 350 PSI. In one embodiment, the solution is pressurized to between about 10 PSI and about 200 PSI. In one embodiment, the solution is pressurized to between about 10 PSI and about 100 PSI. In one embodiment, the solution is pressurized to between about 10 PSI and about 50 PSI. In one embodiment, the solution is pressurized to between about 100 PSI and about 350 PSI. In one embodiment, the solution is pressurized to between about 200 PSI and about 350 PSI. In one embodiment, the solution is pressurized to between about 300 PSI and about 350 PSI. In one embodiment, the solution is pressurized to between about 100 PSI and about 200 PSI. In one embodiment, the apparatus includes air injection and application of pneumatic pressure on fluid in the pressure chamber.

In one embodiment, the solution is pressurized to a negative pressure. In one embodiment, the solution is pressurized to between about −5 and −250 mmHg. In one embodiment, the solution is pressurized to between about −10 and −240 mmHg. In one embodiment, the solution is pressurized to between about −20 and −230 mmHg. In one embodiment, the solution is pressurized to between about −30 and −220 mmHg. In one embodiment, the solution is pressurized to between about −40 and −210 mmHg. In one embodiment, the solution is pressurized to between about −50 and −200 mmHg.

The MNB solution generated by the apparatus is supplied to treatment applicator 150. In some embodiments of the invention, treatment applicator 150 delivers a MNB solution to a surface in need of treatment, such as a wound on a patient's skin. In one embodiment, treatment applicator 150 soaks a tissue in a MNB solution. In one embodiment, treatment applicator 150 rinses a tissue with a MNB solution. In one embodiment, the treatment applicator has one or more outlets connected to a vacuum source. In one embodiment, the vacuum source connected to the treatment applicator is a negative pressure vacuum source.

In some embodiments of the invention, treatment applicator 150 comprises a wound dressing. In one embodiment of the invention, treatment applicator 150 comprises a dressing capable of supplying a MNB solution to the surface of a tissue. In some embodiments, treatment applicator 150 comprises a dressing capable of applying a negative pressure to the surface of a tissue. As is known by one of ordinary skill in the art, the type of dressing to be used depends on the type of wound, clinical objectives, and patient. In one embodiment, treatment applicator 150 comprises an air-tight dressing. In one embodiment, treatment applicator 150 comprises an occlusive dressing. In one embodiment, treatment applicator 150 further comprises low-density foam. In one embodiment, treatment applicator 150 comprises an air-permeable dressing. In one embodiment, the treatment applicator comprises a saturated dressing. In one embodiment, treatment applicator 150 comprises a wound exudate collection system.

In some embodiments, treatment applicator 150 comprises a hydrosurgery system. A hydrosurgery system simultaneously applies a solution and a vacuum to a surface in order to rinse or to debride a wound with continuous flow. In one embodiment, the vacuum is a negative pressure vacuum. In one embodiment, the pressure of the solution and the strength of the vacuum can be modulated to control the degree of wound debridement. In one embodiment, the liquid pressure and applied vacuum levels are low and the degree of wound debridement is low, i.e. a wound rinse. In another embodiment, the liquid pressure and applied vacuum is higher and the wound is debrided. In one embodiment, treatment applicator 150 comprises a hydrosurgery system application wand. In one embodiment, treatment applicator 150 comprises a lavage system application wand. In one embodiment, treatment applicator 150 comprises a micro-nanobubble generator within the application wand. In another embodiment, the treatment applicator is a saturated dressing exposed to room air. In another embodiment, the treatment applicator incorporates the decompression nozzle. In another embodiment, generation is monitored by one or more sensors and used to maintain generation in a feedback servomechanism configuration affecting generation flow, pressure, and nozzle configuration to maintain consistent micro-nanobubble generation parameters and consistent output.

In some embodiments, treatment applicator 150 comprises a vessel capable of containing a MNB solution and a tissue such that contact is maintained between the tissue and the MNB solution. In one embodiment, the tissue is submerged in the MNB solution. In one embodiment, the vessel is air-tight. In one embodiment, the vessel is open to the air. In one embodiment, the vessel comprises an outlet. In one embodiment, the MNB solution is added to the vessel at the same rate at which it drains to give a continuous rinse of MNBs. In one embodiment, a slight negative pressure is applied to the vessel to maintain a continuous flow of a MNB solution over a tissue. In one embodiment, the slight negative pressure is between −50 to −200 mmHg. In one embodiment, the slight negative pressure is between −60 to −190 mmHg. In one embodiment, the slight negative pressure is between −70 to −180 mmHg. In one embodiment, the slight negative pressure is between −70 to −170 mmHg. In one embodiment, the slight negative pressure is between −70 to −160 mmHg. In one embodiment, the slight negative pressure is between −75 to −155 mmHg. In one embodiment, the slight negative pressure is between −80 to −150 mmHg.

Treatment applicator 150 is connected to apparatus 100 via fluid line couplings 149 and 152. Fluid line couplings 149 and 152 can be any fluid line couplings known to those of ordinary skill in the art, such as Luer-Lock, bayonet, screw-connect, or quick release fittings. In one embodiment, fluid line couplings 149 and 152 comprises Luer Lock fittings. In one embodiment, fluid line couplings 149 and 152 comprises bayonet fittings. In one embodiment, fluid line couplings 149 and 152 comprises screw-connect fittings. In one embodiment, fluid line couplings 149 and 152 comprises quick release fittings.

Figure 2:
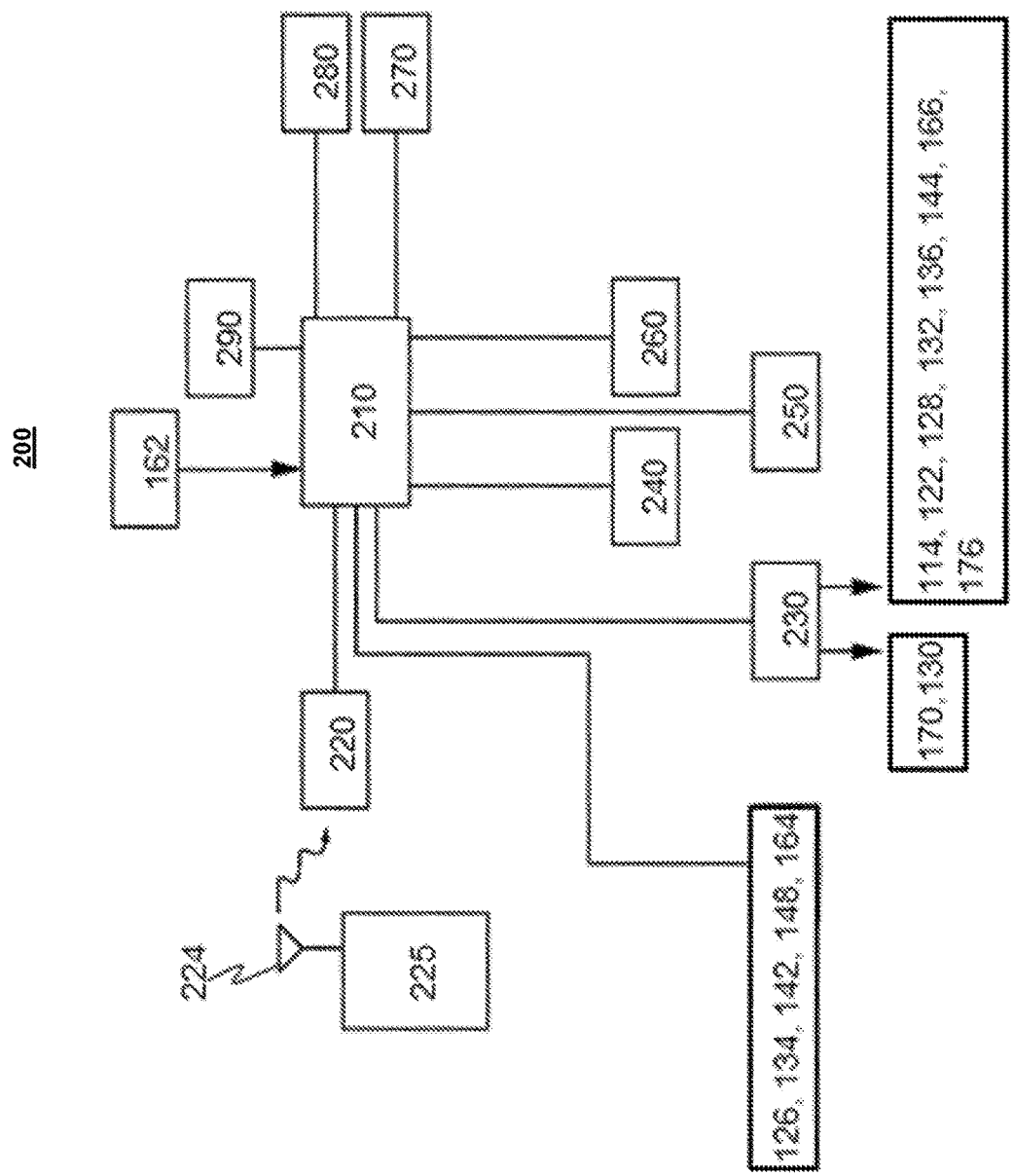
FIG. 2 is a block diagram of an exemplary control system for a MNB generation apparatus.

Waste drained/collected from treatment applicator 150 is collected in main collection chamber 160. In one embodiment, main collection chamber 160 comprises level sensor 162 which relays the volume of main collection chamber 160 to system 200 (FIG. 2). In one embodiment, main collection chamber 160 is open to the air during operation of apparatus 100. In another embodiment, main collection chamber 160 is sealed to the air during operation of apparatus 100. In one embodiment, waste collected in main chamber 160 that is not harvested is transferred to purge waste container 180.

In some embodiments of the invention, a negative pressure is maintained by vacuum source 170. In one embodiment, vacuum source 170 is a negative pressure vacuum source. In some embodiments of the invention, the negative pressure vacuum source employs active regulation of negative pressure vacuum pressure using feedback control. Vacuum source 170 may comprise a continuous pump, a peristaltic pump, a diaphragmatic pump, or any other suitable mechanism for reducing pressure. Vacuum source 170 may comprise a miniature pump or micropump that may be biocompatible and adapted to maintain or draw adequate and therapeutic vacuum levels. The vacuum level of subatmospheric pressure achieved may be in the range of about 5 mmHg to about 760 mmHg. In some embodiment of the invention, the vacuum level is about 20 mmHg to about 500 mmHg, or about 100 mmHg to about 500 mmHg, or about 5 mmHg to about 100 mmHg, or about 500 mmHg to about 760 mmHg. In some embodiments of the invention, the vacuum level may be about 5 to 20 mmHg, or about 20 mmHg to about 100 mmHg, or about 100 mmHg to about 300 mmHg, or about 300 to about 500 mmHg, or about 500 to about 600 mmHg, or about 600 to 760 mmHg.

In some embodiments of the invention, vacuum source 170 is connected to main collection chamber 160 via secondary collection chamber 168. Secondary collection chamber 168 captures any particulate matter or liquid to insure continuous operation of vacuum source 170. In one embodiment, collection chamber 168 is disposable. In another embodiment, chamber 168 comprises multiple chambers in serial.

The direction of flow of liquids is maintained through check valves 112, 129, 133, 138, 146, and 178. As contemplated herein, a check valve may be any type of one-way, self-actuating valve used to permit fluid flow in only one direction. The check valves can be of any construction known to those in the art, including, but not limited to, diaphragm check valves, swing check valves, piston lift valves, ball check valves, umbrella valves, stop-check valves, in-line check valves, duckbill valves, pneumatic non-return valves, and duo check valves.

Liquid flow between components within apparatus 100 can be controlled by control system 200 through independent operation of solenoid valves 114, 122, 128, 132, 136, 144, 166, and 176, and pressure levels at various points in the apparatus can be determined via inline pressure sensors 126, 134, 142, 148, and 164 that provide information to control system 200. In one embodiment, solenoid valves 114, 122, 128, 132, 136 and the properties of the decompression nozzle 124 can be altered by a control system with input from pressure, flow, dissolved oxygen, turbidity, galvanic particle counters, and other sensors in addition to knowledge of system operation parameters and past history of operation (i.e. self-learning).

In some embodiments, apparatus 100 comprises a counting unit for counting micro-nanobubbles. In one embodiment, the counting unit comprises a light source. In one embodiment, the light source is a laser source. In one embodiment, the light source is a halogen light. In one embodiment, the counting unit comprises a particle counter. In one embodiment, the counting unit comprises a particle sizer. In one embodiment, the counting unit comprises a diffusion charger. In one embodiment, the counting unit comprises a low pressure impactor.

In some embodiments, apparatus 100 comprises a safety mechanism. In one embodiment, the safety mechanism automatically turns the apparatus off. In one embodiment, the safety mechanism comprises a button that can be operated by a user to turn the apparatus off.

Exemplary apparatus 100 may be controlled by exemplary control system 200 (FIG. 2). Control system 200 comprises a central microcontroller board 210. In one embodiment, board 210 provides logical control based on an Atmel ATmega2560 or similar microcontroller, a microprocessor, a commercially available programmable logic controller, or an Field Programmable Gate Array (FPGA), or any other board/chipset known to those of skill in the art. In one embodiment, board 210 is programmable and has multiple input/output connections.

Computer system 225 controls the operation of the system via a connection to microcontroller board 210. The computer system 225 may comprise any computer system or visual user interface known to those in the art. In one embodiment, software configured to interface with microcontroller board 210 is controlled via computer system 225. In one embodiment, computer system 225 comprises standard inputs such as a keyboard and a mouse and standard outputs such as a display panel and communication ports. In one embodiment, computer system 225 comprises a laptop computer. In one embodiment, computer system 225 comprises a tablet computer or smartphone. In one embodiment, computer system 225 comprises an industrial display panel providing a graphical or textual user interface.

Microcontroller board 210 is connected to computer system 225 via communication system 220 and 224. In one embodiment, communication system 220 and 224 comprises a cable connecting controller board 210 to computer system 225. In another embodiment, communication between board 210 and computer system 225 is wireless. In one embodiment, communication system component 220 is a wireless receiver connected to board 210 via a serial connection. In one embodiment, the wireless method of communication is Bluetooth® (BT)/Bluetooth Low Energy® (BLE) and communication system component 220 comprises a commercial BT serial/UART interface board. In one embodiment, computer system 225 comprises a wireless transmitter 224. In one embodiment, wireless transmitter/receiver 224 is a BT transmitter.

In one embodiment, microcontroller board 210 receives feedback from exemplary apparatus 100 via analog or digital connections to inline pressure sensors 126, 134, 142, 148, and 164 as well as level sensor 162.

Microcontroller board 210 is connected to relay boards 230 via general purpose input/output (GPIO) connectors, which allows for control of pumps 130 and 170 and independent operation of solenoid valves 114, 122, 128, 132, 136, 144, 166, and 176.

In one embodiment of the invention, microcontroller board 210 is connected to rotary input 240. In one embodiment, rotary input 240 supplies commands independent of computer system 225.

In one embodiment of the invention, microcontroller board 210 is connected to pressure switch 250. In one embodiment, pressure switch 250 is foot-controlled, allowing for hands-free control of apparatus 100. In one embodiment, pressure switch 250 comprises a momentary action pedal; constant pressure is required to maintain operation of the apparatus. In another embodiment, pressure switch 250 comprises a potentiometer foot pedal that allows for precise modulation of apparatus operation parameters such as air pressure and vacuum level.

Microcontroller board 210 receives input via push buttons 260. In one embodiment, push buttons 260 control operation mode, such as normal operation, purge, emergency stop, pressurize, and the like. In one embodiment, push buttons 260 connect to microcontroller board 210 via general purpose digital or analog interfacing.

In one embodiment, auditory operational alerts are produced by sounding system 270. In one embodiment, sounding system 270 is a piezoelectric speaker. In one embodiment, sounding system 270 is connected to microcontroller 210 via a pulse width modulating connector.

In one embodiment, control system 200 is connected to at-a-glance indicators 280. In one embodiment, at-a-glance indicators 280 comprise light-emitting diodes (LEDs). In one embodiment, indicators 280 are connected to microcontroller board 210 via general purpose digital or analog interfacing.

In one embodiment of the invention, control system 200 comprises status panel 290. In one embodiment, status panel 290 is connected to microcontroller 210 via a serial cable. In one embodiment, status panel 290 displays short status messages.

Operation of the Apparatus

In one embodiment of the invention, apparatus 100 functions as a hydrosurgery system, supplying MNBs to the surface of a tissue during tissue debridement. In a non-limiting example of such a procedure, liquid source 110 supplies purified or sterilized water or a saline solution to micro-nanobubble generation pump 120 via check valve 112 and open solenoid valve 114. At the same time, gas inlet 116 supplies metered oxygen gas to micro-nanobubble generation pump 120. Micro-nanobubble generation pump 120 creates an optically dense solution of microbubbles that pass through open solenoid valve 122 and decompression nozzle 124. Decompression nozzle 124 converts the microbubbles to micro-nanobubbles. Positive pressure is applied to the apparatus via air pump 130. The pressure delivered by pump 130 is monitored by in-line pressure sensor 134 and modulated by microcontroller 210 via interface with relay board 230. In one embodiment, a second decompression nozzle is located beyond decompression nozzle 124 in the fluid flow pathway. Solenoid valves 132 and 128 are closed during normal operation. The apparatus is pressurized by pressure chamber 140. The pressurized MNB solution is supplied to treatment applicator 150. Conventional hydrosurgery systems utilize simultaneous application of pressurized solution and vacuum suction to debride wound surfaces via sheer forces and the Venturi effect. Micro- or nanobubble solutions provide additional bi-phasic effects and flocculation to improve debris removal. In this non-limiting example of apparatus operation, the vacuum is applied by vacuum source 170. Treatment applicator 150 creates a steady stream of MNB solution that debrides surface tissue. Waste from the debridement process is collected in main collection chamber 160, the volume of which is monitored by level sensor 162 which is relayed to control system 200 via relay board 230. During normal operation of the apparatus, solenoid valve 176 is closed. Between vacuum source 170 and main collection chamber 160 is secondary collection chamber 168, which helps to maintain the integrity of the vacuum source. In some embodiments, vacuum source 170 is a negative pressure vacuum source.

In one embodiment of the invention, apparatus 100 functions as a negative pressure wound therapy (NPWT) system, which involves the controlled application of subatmospheric pressure to the wound environment followed by delivery of a MNB solution to irrigate the wound. In one embodiment, rounds of negative pressure and MNB irrigation are alternating. In another embodiment, MNB irrigation and negative pressure application are simultaneous, creating a continuous flow of a MNB solution over the tissue. In a non-limiting example of NPWT using apparatus 100, solenoid valves 144 and 178 are closed and solenoid valve 128 is opened, so that the MNB solution is not directed toward treatment applicator 150 and the negative pressure is maintained. In this non-limiting example, treatment applicator 150 consists of an air-tight dressing such as that known to one of ordinary skill in the art. A vacuum is applied to treatment applicator 150 and any exudate is collected in main collection chamber 160. Following a predetermined period of negative pressure, solenoid valves 128 and 166 are closed and solenoid valve 144 is opened, so that a MNB solution is supplied to treatment applicator 150. The NPWT treatment comprises alternating periods of negative pressure and MNB solution rinse.

In one embodiment of the invention, apparatus 100 functions as a NPWT system in which continuous MNB solution and vacuum is applied. In a non-limiting example of such a procedure, liquid source 110 supplies a saline solution to micro-nanobubble generation pump 120 via check valve 112 and open solenoid valve 114. At the same time, gas inlet 116 supplies oxygen gas to micro-nanobubble generation pump 120. Micro-nanobubble generation pump 120 creates an opaque solution of microbubbles that pass through open solenoid valve 122 and decompression nozzle 124. Decompression nozzle 124 converts the microbubbles to micro-nanobubbles. Positive pressure is applied to the apparatus via air pump 130. The pressure delivered by pump 130 is monitored by in-line pressure sensor 134 and modulated by microcontroller 210 via interface with relay board 230. Solenoid valves 132 and 128 are closed during normal operation. The apparatus is pressurized by pressure chamber 140. The pressurized MNB solution is supplied to treatment applicator 150, which, in this non-limiting example, is an air-tight wound dressing. Concurrent to MNB solution rinse, a negative pressure is applied by vacuum source 170; the result is a continuous flow of MNB solution over the treatment area. Waste from the NPWT is collected in main collection chamber 160, the volume of which is monitored by level sensor 162 which is relayed to control system 200 via relay board 230. During normal operation of the apparatus, solenoid valve 176 is closed. Between vacuum source 170 and main collection chamber 160 is secondary collection chamber 168, which helps to maintain the integrity of the vacuum source.

In one embodiment of the invention, apparatus 100 creates a MNB solution for rinsing tissue that has been removed from a subject, wherein constant contact is maintained between the tissue and the MNB solution. In a non-limiting example of this application of apparatus 100, treatment applicator 150 is a vessel containing tissue for transplant or grafting. Treatment applicator 150 may optionally include an outlet port for collecting soiled solution and allowing for constant refreshing of the MNB solution. In this non-limiting example, solenoid valves 166, 132, and 128 are closed and solenoid valves 114, 122, 136, 144, and 176 are open. The MNB solution generating by passing a liquid from liquid source 110 and a gas from gas inlet 116 through micro-nanobubble generation pump 120 and decompression nozzle 124 is pressurized by air pump 130 and pressure chamber 140 and delivered to the treatment applicator 150, a vessel containing a tissue and an outlet port. If a negative pressure is needed to ensure the continuous flow of the MNB solution, solenoid valve 176 can be closed and solenoid valve 166 opened. In some embodiments, system elements related to the application of negative pressure vacuum to recover applied fluid is not present.

Treatment Solutions

In one aspect of the invention, gas inlet 116 is connected to a gas source such as a gas tank or a gas compressor/generator/concentrator. Examples of suitable gases include helium, nitrogen, carbon dioxide, carbon monoxide, ambient air (such as from a compressed air tank or an air compressor system), hydrocarbons, fluorocarbons, hydrofluorocarbons, chlorofluorocarbons, oxygen, ozone, and combinations thereof. In one embodiment, the gas comprises oxygen. In one embodiment, the gas comprises ozone. In one embodiment, the gas comprises ambient air. In one embodiment, the gas comprises about 5% ozone in about 95% oxygen. In one embodiment, the gas comprises about 4% ozone in about 96% oxygen. In one embodiment, the gas comprises about 3% ozone in about 97% oxygen. In one embodiment, the gas comprises about 2% ozone in about 98% oxygen. In one embodiment, the gas comprises about 1% ozone in about 99% oxygen. In one embodiment, the gas comprises about 0.5% ozone in about 99.5% oxygen. In one embodiment, the gas consists of oxygen.

The gas and liquid are combined within apparatus 100 to produce a gas/liquid mixture comprising micro-nanobubbles (MNBs). As contemplated herein, liquid source 110 may supply any liquid capable of maintaining the composure of the MNBs. In some embodiments, the liquid comprises one or more additives that increase the stability of the MNBs in solution or confer additional beneficial properties to the liquid. For example, in one embodiment, it might be desirable to include an additive that confers additional health benefits to the liquid. In one embodiment, the additive increases the stability of the MNBs. In another embodiment, the additive maintains the buffering capacity of the liquid.

The liquid used can be any solvent or solution that supports the formation and preservation of MNBs. In one embodiment, the liquid source comprises any physiologically compatible aqueous buffer solution known to those of skill in the art. Non-limiting solutions include Hank's solution, Ringer's solution, saline, ringers lactate, D5W, transplant preservation solutions, and buffer solutions such as boric acid, sodium and potassium bicarbonate, sodium and potassium borates, sodium and potassium carbonate, sodium acetate, sodium biphosphate and the like. In one embodiment, the liquid source comprises recirculated fluid from the system containing micro-nanobubbles. In one embodiment, the liquid source comprises deionized and/or sterilized water. In one embodiment, the liquid source comprises purified water. In one embodiment, the liquid source comprises a sterile saline solution. In one embodiment, the liquid source comprises normal saline (0.9% NaCl in sterile water). In one embodiment, the liquid source comprises half-normal saline.

In some embodiments, the liquid comprises water and at least one additive. In one embodiment, the additive comprises a second liquid such as a solvent. In one embodiment, the solvent is miscible in water. Exemplary additive solvents include, but are not limited to, acetic acid, acetone, acetonitrile, tert-butyl alcohol, diethylene glycol dimethyl ether (diglyme), 1,2-dimethoxyethane (glyme), dimethylformamide, dimethylsulfoxide, 1,4-dioxane, ethanol, ethylene glycol, glycerin, hexamethylphosphoramide, hexamethylphosphorous triamide, methanol, n-propanol, and iso-propanol, and any combination thereof.

In one embodiment, the additive comprises an electrolyte. Non-limiting examples of electrolytes include organic salts, inorganic salts, and mixtures thereof, as well as polyelectrolytes, such as uncapped polyacrylates, polymaleates, or polycarboxylates, lignin sulfonates or naphthalene sulfonate formaldehyde copolymers. The electrolyte typically comprises a salt having a cationic component and an anionic component. Suitable cations may be monovalent or multivalent, may be organic or inorganic, and include, for example, sodium, potassium, lithium, calcium, magnesium, cesium, and lithium cations, as well as mono-, di- tri- or quaternary ammonium or pyridinium cation. Suitable anions may be a monovalent or multivalent, may be organic or inorganic and include, for example, chloride, sulfate, nitrate, nitrite, carbonate, citrate, cyanate acetate, benzoate, tartarate, oxalate, phosphate, and phosphonate anions. Suitable electrolytes include, for example, salts of multivalent anions with monovalent cations, such as potassium pyrophosphate, potassium tripolyphosphate, and sodium citrate, salts of multivalent cations with monovalent anions, such as calcium chloride, calcium bromide, zinc halides, barium chloride, and calcium nitrate, and salts of monovalent cations with monovalent anions, such as sodium chloride, potassium chloride, potassium iodide, sodium bromide, ammonium bromide, alkali metal nitrates, and ammonium nitrates.

In one embodiment, the additive comprises one or more pharmaceutically acceptable buffering agents. Illustrative examples of specific buffering agents include, without limitation, aluminum hydroxide, aluminum hydroxide/magnesium carbonate, aluminum hydroxide/magnesium carbonate/calcium carbonate co-precipitate, aluminum magnesium hydroxide, aluminum hydroxide/magnesium hydroxide co-precipitate, aluminum hydroxide/sodium bicarbonate coprecipitate, aluminum glycinate, calcium acetate, calcium bicarbonate, calcium borate, calcium carbonate, calcium citrate, calcium chloride, calcium gluconate, calcium glycerophosphate, calcium hydroxide, calcium lactate, calcium phthalate, calcium phosphate, calcium succinate, calcium tartrate, dibasic sodium phosphate, dipotassium hydrogen phosphate, dipotassium phosphate, disodium hydrogen phosphate, disodium succinate, dry aluminum hydroxide gel, L-arginine, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium dihydrogen phosphate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tetrasodium pyrophosphate, trihydroxymethylaminomethane, tripotassium phosphate, trisodium phosphate, and trometamol, and mixtures thereof. (Based in part upon the list provided in *The Merck Index*, Merck & Co. Rahway, N.J. (2001)). In addition, proteins or protein hydrolysates can serve as buffering agents owing to their ability to rapidly neutralize acid.

In one embodiment, the additive comprises agents that modify micro-nanobubble generation properties by modification of the generation process by changing fluid properties (density, hydrogen boding forces, conductivity, etc.) and affect the coalescence, re-forming, nucleation, or growth of generated bubbles. These agents may include dextran, chitosan, pH modifiers/buffers, alcohols including (but not limited to) ethanol and glycol, surfactants, organic or inorganic colloids, metal colloids including nano-crystline silver, gold, and zinc, polymeric viscosity modifiers. In addition to modifying generation, bubbles may act as carriers for added agents to tissue.

In one embodiment, the liquid comprises at least one antimicrobial agent. Non-limiting examples of antimicrobial agents include levofloxacin, doxycycline, neomycin, clindamycin, minocycline, gentamycin, rifampin, chlorhexidine, chloroxylenol, methylisothizolone, thymol, α-terpineol, cetylpyridinium chloride, hexachlorophene, triclosan, nitrofurantoin, erythromycin, nafcillin, cefazolin, imipenem, astreonam, gentamicin, sulfamethoxazole, vancomycin, ciprofloxacin, trimethoprim, rifampin, metronidazole, clindamycin, teicoplanin, mupirocin, azithromycin, clarithromycin, ofaxocin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linexolid, temafloxacin, tosufloxacin, clinafloxacin, sulbactam, clavulanic acid, amphotericin B, fluconazole, itraconazole, ketoconazole, nystatin, penicillins, cephalosporins, carbepenems, beta-lactams antibiotics, aminoglycosides, macrolides, lincosamides, glycopeptides, tetracyclines, chloramphenicol, quinolones, fucidines, sulfonamides, trimethoprims, rifamycins, oxalines, streptogramins, lipopeptides, ketolides, polyenes, azoles, echinocandins, and any combination thereof.

In some embodiments, the liquid comprises a solution used by those of skill in the art to prolong the viability of tissues removed from a body. Exemplary solutions include Carolina rinse, Ringer's solution, BASE, UW solution (with or without hydroxyethyl starch), EuroCollins solution, Ross-Marshall citrate solutions, Bretschneider histidine tryptophan ketoglutarate solution, phosphate-buffered sucrose, Celsior solution, Kyoto ET solution, water, normal saline, half-normal saline, ringers lactate, D5W, transplant preservation solutions, and histidine tryptophan ketoglutarate solution.

In some embodiments, the liquid comprises an anti-septic solution used for wound irrigation. Exemplary solutions include PHMB/biguanides (Prontosan), hypochlorite solutions (Dermacyn), hypochlorous acid solutions, solutions of oxidized water, sodium hypochloride and hypochlorous acid, sulfur based solutions/sulfonamides, biguanides (polyhexanide), isotonic saline, lidocaine HCL, acetic acid, 1% povidone-iodine solution, pluronic F-68, hydrogen peroxide solutions, and the like.

Methods of the Invention

In one aspect, the present invention relates to a method of treating a tissue with a treatment solution comprising micro-nanobubbles. An exemplary method comprises the steps of providing a flow of liquid from a liquid source, introducing a gas from a gas source into the flow of liquid to create a gas/liquid mixture, passing the gas/liquid mixture through a micro-nanobubble generation pump, passing the gas/liquid mixture through a decompression nozzle, thereby generating micro-nanobubbles in the gas/liquid mixture, introducing the gas/liquid mixture having the micro-nanobubbles into a treatment applicator, and contacting a target tissue with the micro-nanobubbles via the treatment applicator.

In some embodiments of the invention, a negative pressure is applied at the treatment applicator. In some embodiments, the negative pressure is applied using a vacuum source connected to the treatment applicator. In some embodiments, applying the negative pressure at the treatment applicator and contacting the target tissue with the micro-nanobubbles via the treatment applicator occurs simultaneously. Such embodiments may be used to maintain a continuous flow of micro-nanobubbles over the tissue to be treated. In some embodiments, a continuous flow of micro-nanobubbles is used to treat a burn wound. In some embodiments, a continuous flow of micro-nanobubbles is used to treat a skin ulcer. In some embodiments, a tissue is placed in a continuous flow of micro-nanobubbles. In some embodiments, a continuous flow of micro-nanobubbles may be used to debride a wound via the Venturi effect, wherein the flow of solution results in a negative pressure exerted in a direction normal to the flow of solution; such a negative pressure may remove exudate from the surface layer of a wound or may remove debris or detritus depending on the magnitude of the negative pressure.

In some embodiments, applying the negative pressure at the treatment applicator occurs after contacting the target tissue with the micro-nanobubbles via the treatment applicator. In one embodiment, the application of negative pressure and contacting the target tissue with the treatment solution comprising micro-nanobubbles is alternated: a negative pressure is applied to the tissue, followed by contact with the treatment solution. In one embodiment, the number of cycles and the duration of each step in the cycle is determined by a treating physician based on the type of tissue and, if applicable, the severity of the wound.

In some embodiments of the invention, the treatment solution comprises a mixture of micro-nanobubbles a physiologic clinical solution. Exemplary physiologic clinical solutions include, but are not limited to, water, normal saline, half-normal saline, ringers lactate, D5W, transplant preservation solutions, and combinations thereof. In one embodiment, the treatment solution further comprises additional additives. In one embodiment, the treatment solution comprises a solution of oxygen micro-nanobubbles in a physiologic clinical solution. In one embodiment, the treatment solution comprises ozone and oxygen micro-nanobubbles in a physiologic clinical solution. In one embodiment, the treatment solution comprises ambient air and oxygen micro-nanobubbles in a physiologic clinical solution. In one embodiment, the treatment solution comprises at least one antimicrobial agent.

In some embodiments of the invention, the tissue to be treated is a tissue that is removed from a subject and then placed into another subject (i.e., allograft tissue) or the same subject (i.e., autograft tissue). In some embodiments, the tissue is an organ. Exemplary organs include, but are not limited to, the heart, kidneys, liver, lungs, pancreas, intestine, thymus, testis, penis, uterus, ovaries, hands, legs, and the face. In some embodiments, the tissue is not an organ. A non-limiting list of tissues includes: corneas, sclerae, skin, bone (including joints), cartilage, ligaments, tendons, heart valves, veins, arteries, islet cells, the middle ear, lipoaspirate, and bone marrow. In some embodiments of the invention, the tissue to be treated is removed from the same subject into which it is placed; such a procedure is often called "autografting". Examples of tissues that may be subjected to grafting include gum tissue, fatty tissue, bone, tendons, ligaments, and skin. In one embodiment, the tissue is fatty tissue. In one embodiment, the tissue is lipoaspirate obtained through liposuction.

In some embodiments of the invention, the tissue to be treated is a wound. Examples of wounds may include both open and closed wounds. Exemplary wounds include burns, incisions, excisions, lacerations, abrasions, puncture or penetrating wounds, surgical wounds pressure sores, vascular ulcers, vasculitis-induced ulcers, arterial ulcers, diabetic foot ulcers, sternal or abdominal wounds, tunneled wounds, chronic wounds, decubitus ulcers, and pyoderma gangrenosum and arthritis-related ulcers. In one embodiment, the tissue is a burn wound. In one embodiment, the tissue is a skin ulcer, such as a diabetic ulcer. In one embodiment, the tissue comprises a wound covered with wound dressing(s). In one embodiment, the tissue comprises a wound covered with dressing and negative pressure. In another embodiment, the tissue comprises ex-vivo tissue including tissues and samples or cultures of lipoaspirate or islet cells.

In some embodiments of the invention, the tissue is contacted with a solution of micro-nanobubbles. In some embodiments, contacting the tissue with the solution of micro-nanobubbles comprises soaking the tissue in the solution of micro-nanobubbles. In another embodiment, contacting the tissue comprises rinsing the tissue in the solution of micro-nanobubbles. In one embodiment, the rinse immediately precedes the closing of a wound, such as in a surgical procedure. In one embodiment, the tissue is placed in a still solution of micro-nanobubbles. In another embodiment, the tissue is placed in a continuous flow of micro-nanobubbles. In one embodiment, the tissue may be perfused with the MNB solution via a vascular route prior to transplantation, such as in the case of organs or replantation of severed limbs or digits.

Kits of the Invention

The invention also includes a kit comprising an apparatus for the generation and administration of a solution of MNBs useful within the methods of the invention and an instructional material that describes, for instance, administering the MNB solution to a tissue in order to treat a wound or a tissue as described elsewhere herein. In one embodiment, the kit comprises sterile consumable components for the generation, delivery, and administration of a solution of MNBs. In one embodiment, the kit comprises sterilizable durable components for the generation, delivery, and administration of a solution of MNBs. In one embodiment, the kit comprises both sterile consumable components and sterilizable durable components. In an embodiment, the kit further comprises a sterile liquid source and a gas source as described herein to produce the MNB solution using the apparatus of the invention. In one embodiment, the kit is packaged for field usage such as in an ambulance.

Those skilled in the art will recognize, or be able to ascertain using no more than routine experimentation, numerous equivalents to the specific apparatuses, methods, embodiments, claims, and examples described herein. Such equivalents were considered to be within the scope of this invention and covered by the claims appended hereto. For example, it should be understood, that modifications of apparatus parameters, including but not limited to pressures, flow rates, and volumes, and appropriate apparatus components, such as connectors, tubing, and containers/vessels, with art-recognized alternatives and using no more than routine experimentation, are within the scope of the present application.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the apparatuses of the present invention and practice the claimed methods. The following working examples therefore, specifically point out various embodiments of the present invention, and are not to be construed as limiting in any way the remainder of the disclosure.

Example 1: Generation of MNBs

Figure 3:
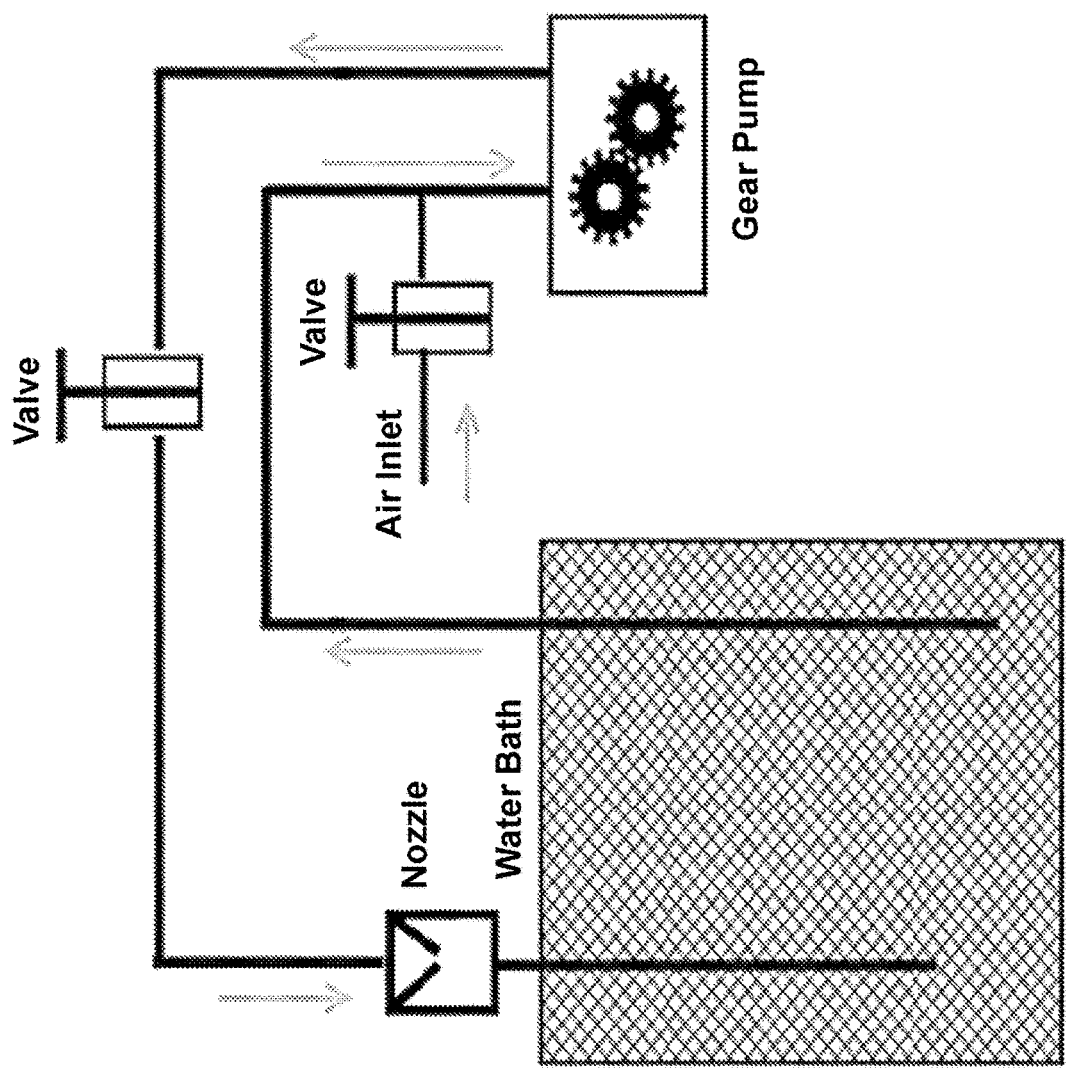
FIG. 3 is a schematic of an exemplary dissolved gas depressurization MNB generator.
Figure 4:
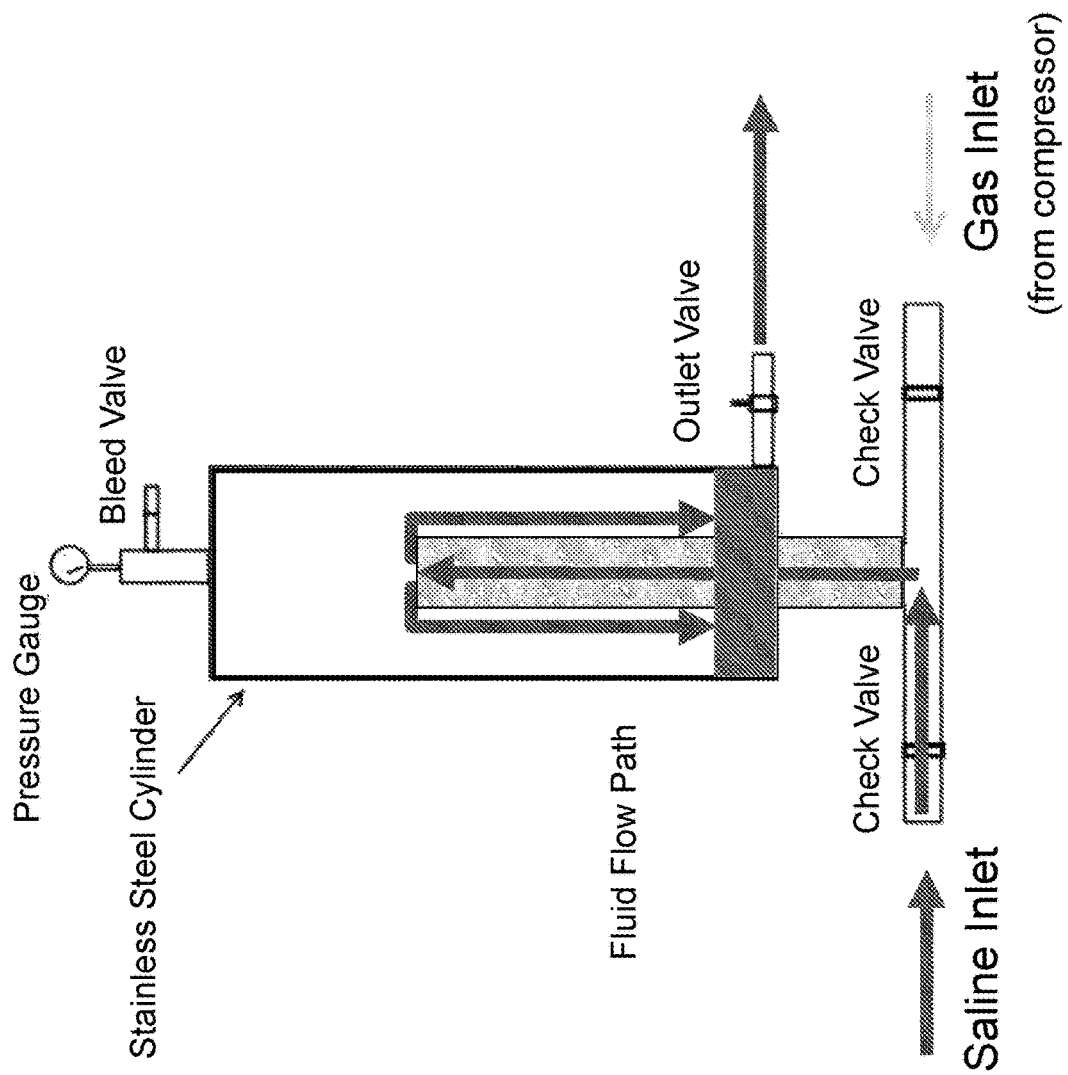
FIG. 4 is a schematic of an exemplary falling film continuous DGD system.
Figure 5:
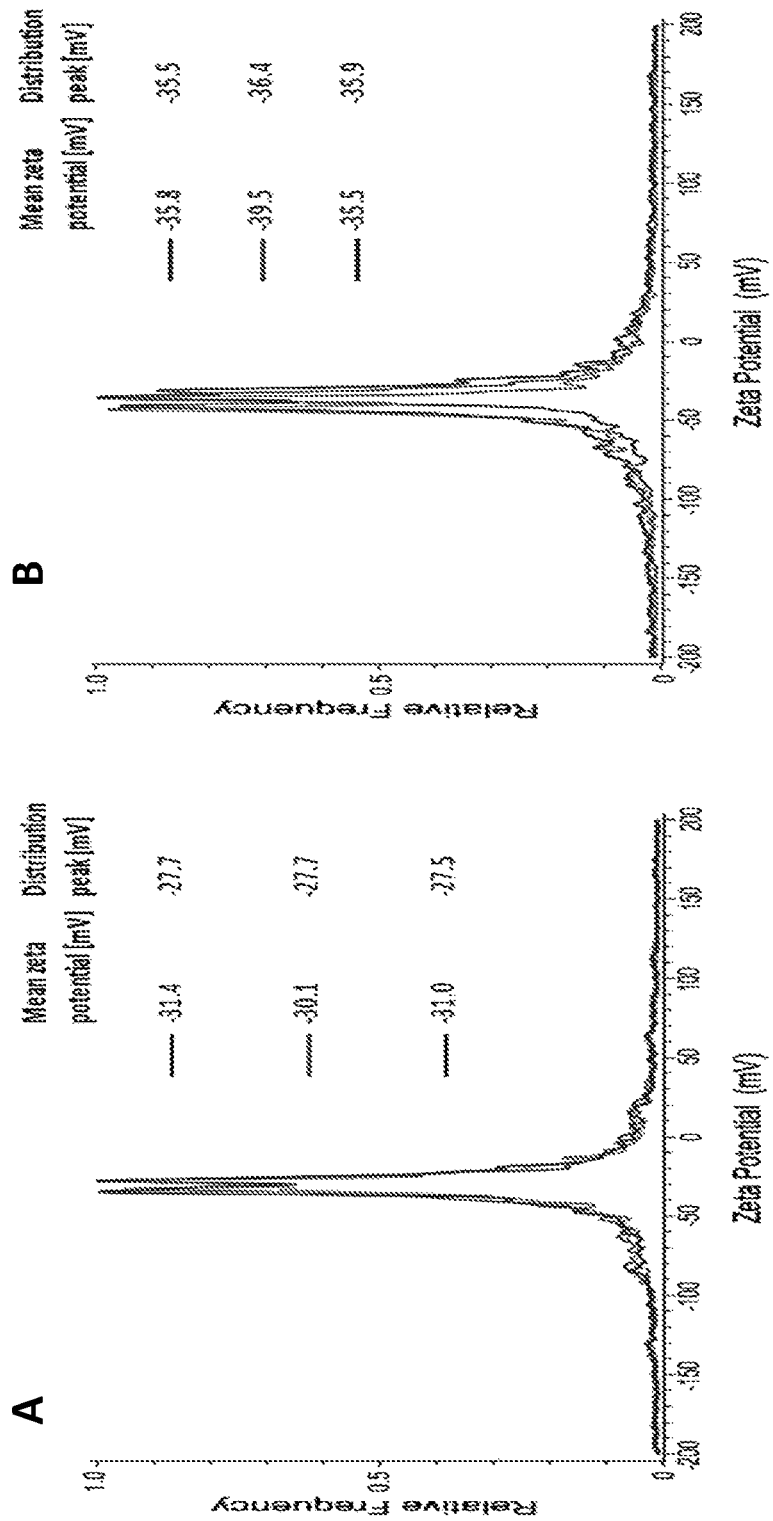
FIG. 5, comprising

MNBs are produced using a well-established dissolved gas depressurization (DGD) method (FIG. 3 and FIG. 4) (Maeda et al., Exp. Therm. Fluid. Sci., 2015, 60, 201-207; Tsuge, H. Micro- and nanobubbles, Pan Stanford Publishing, 2014) where strong static alternating magnetic or electric fields (AMF) can be used to assist the generation of micro-nanobubbles. This system can be used to assist micro-nanobubble generation or distribution control within the generation and collection system. This approach may be used in the decompression nozzle or distal or proximal to this system component. Zeta potential measurements (FIG. 5) compare MNBs produced using the DGD method and using AMF treated deionized water.

Example 2: Measuring the $pO_2$ in Oxygenated MNB Solutions

MNBs were created in normal saline (NS, 0.9% NaCl) using a dissolved gas depressurization (DGD) method (Maeda et al., Exp. Therm. Fluid. Sci., 2015, 60, 201-207). DGD was implemented in the present work using a system developed by Li and Klopfer (Klopfer, Micro and Nanobubbles for Wound Healing Applications: University of California, Irvine; 2015). The baseline saline solution was chilled to 4° C. and was then pressurized at 700 kPa of pure oxygen for 10 minutes. Rapid decompression through an engineered expansion orifice results in the production of the microbubble solution. The dispersion of the microbubbles results in a solution containing nanobubbles. Solution $pO_2$ levels were measured using conventional Winkler titration, polarography, and a novel method using oxygen-sensitive microparticles (OSMs) that were encapsulated in alginate beads. For this method, the OSM particles were compounded with polystyrene beads (average MW=2500) and ultrasonicated in an alginate solution (2.5% low viscosity mannuronate, Novamatrix, Norway) to create a homogenous suspension. The beads were created by running the alginate-OSM suspension through an electrostatic gas-driven encapsulator (Nisco Engineering AG, Switzerland). Using an electro-optical probe, the OSMs were excited, and the emitted light was recorded to determine the $pO_2$ levels following the protocol described by Weidling et al. (J. Biomed. Opt., 2014, 19, 087006). All of the samples were kept at room temperature (25° C.) while the $pO_2$ was measured. This technique was used to measure the oxygenation levels within the nanobubbled solution as follows.

Figure 6:
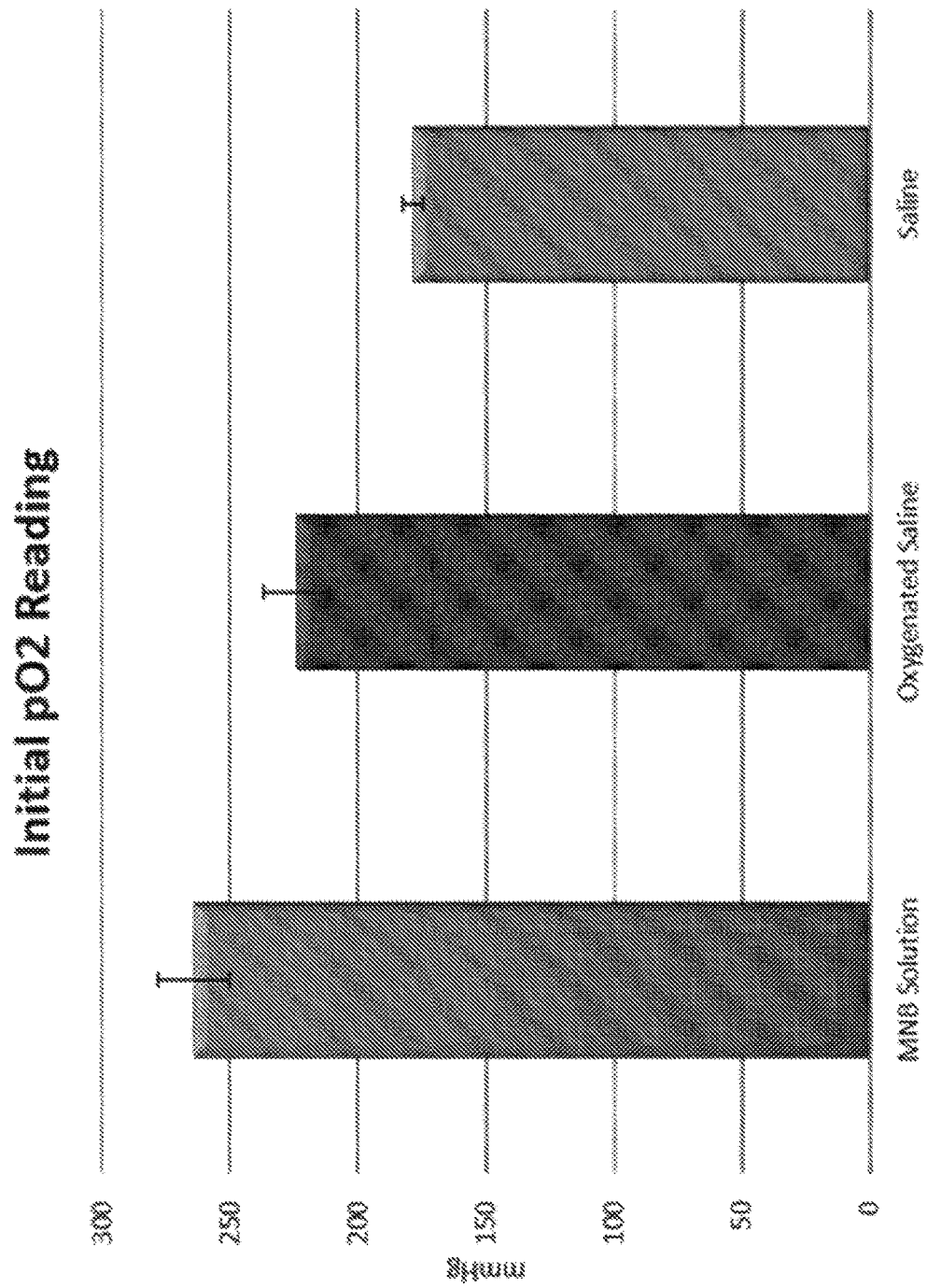
FIG. 6 is a plot of the initial $pO_2$ values of a solution of MNBs in normal saline (NS) solution compared to that of oxygenated saline and untreated saline.

The MNB solution, oxygenated saline (OS) and normal saline (NS) samples were used to measure the $pO_2$. As expected, the MNB solution consistently had the highest initial $pO_2$, followed by the OS and NS (264 mmHg, 223 mmHg and 178 mm Hg on average, respectively). The differences between the groups were statistically significant (by a one-way ANOVA test—P value 0.001) (FIG. 6).

Figure 7:
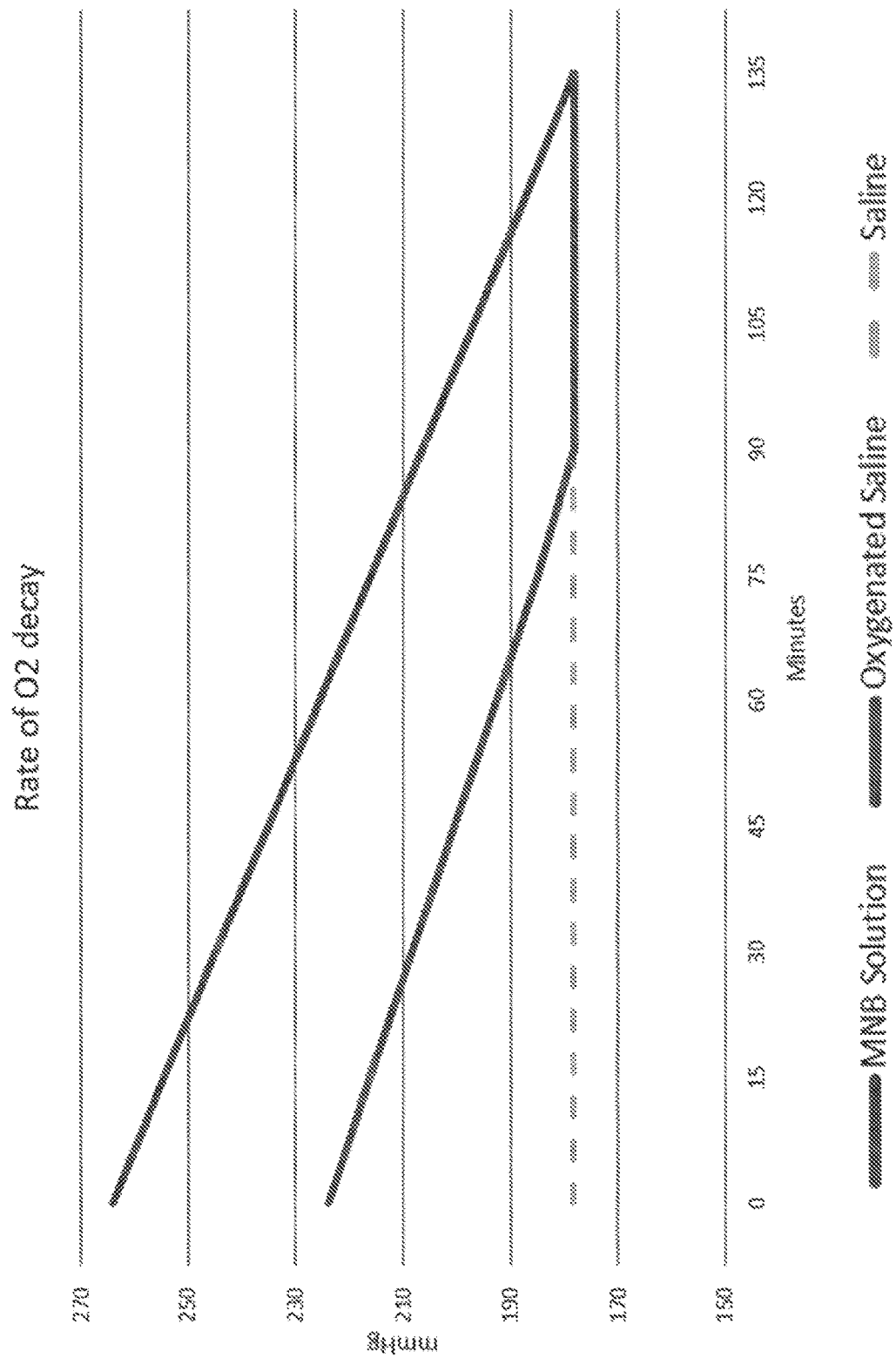
FIG. 7 is a plot of the decay in $pO_2$ of a MNB solution in saline compared to that of oxygenated saline and an untreated saline solution.

To verify that the MNB solution is an efficient oxygen transporter capable of retaining oxygen and remaining stable for extended periods of time, the alginate bead method described above was employed. The $pO_2$ of the MNB solution, the OS and the NS were measured for over a period >2 hours. The average rates of decay for the solutions were as follows: −0.640 mmHg/min for MNBs; −0.522 mmHg/min for OS and −0.024 mmHg/min for saline (FIG. 7). Extrapolating these results, it will take approximately 133 min for the $pO_2$ of the MNB solution to reach the NS $pO_2$ level. This is 1.8 times longer than it would take for the OS to reach the NS $pO_2$ level. Since the OS is capable of improving tissue oxygenation, we can deduce that the MNB solution will yield clinically relevant increases in tissue oxygenation.

Example 3: Measuring $pO_2$ in Tissue

Figure 8:
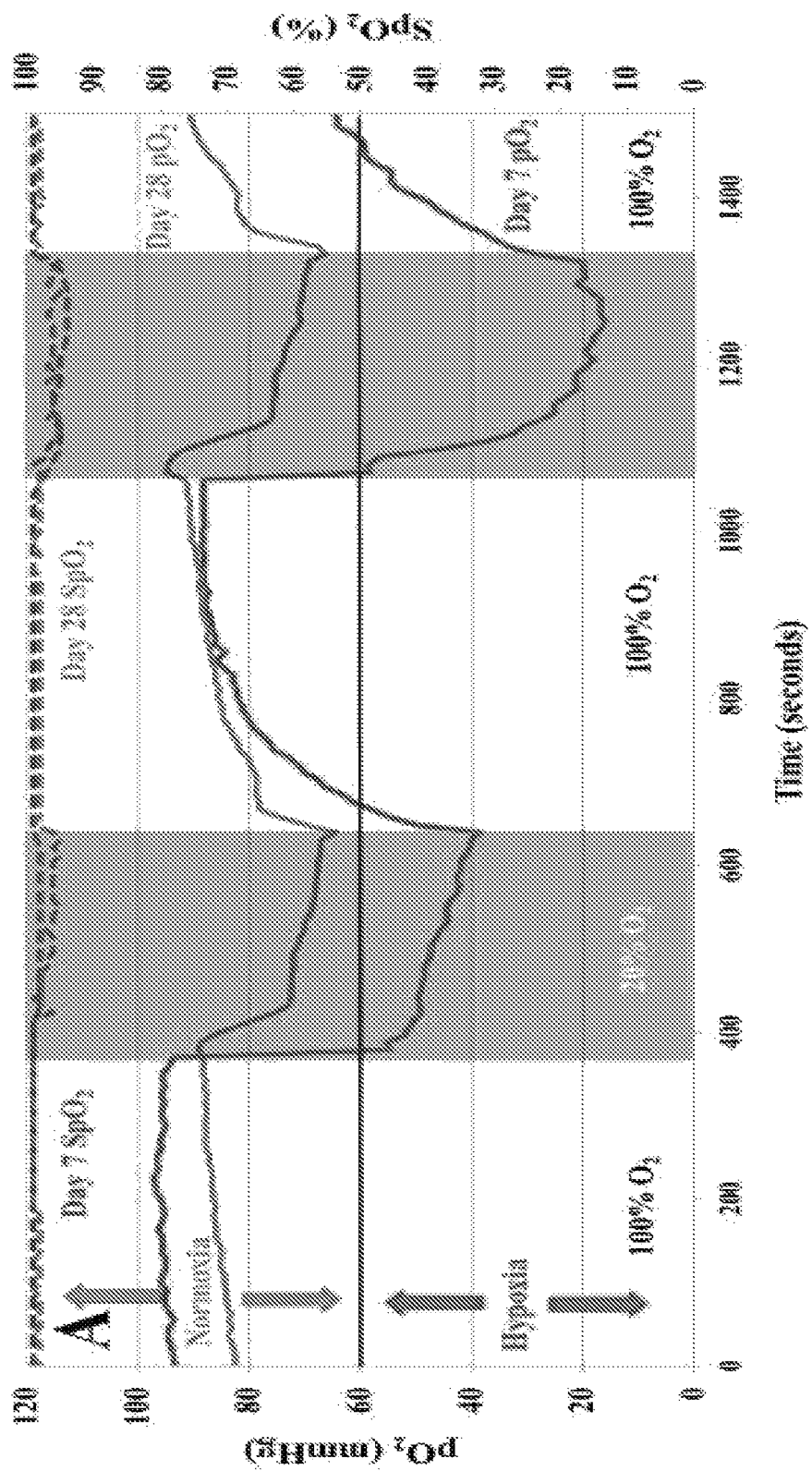
FIG. 8 depicts the results of a noninvasive evaluation of oxygen tension in subcutaneous implants. Changes in oxygen tension ($pO_2$) within subcutaneously-implanted devices were monitored 7 days and 28 days after implantation.

A major challenge in determining the benefits of varied forms of $O_2$ therapeutics and delivery systems relates to the difficulty in the measurement of $O_2$ tension in the tissues surrounding the wound. To address the latter problem, an original topical $O_2$ tension measurement system was developed using specific oxygen-sensing microparticles (OSMs). A novel imaging modality was utilized to noninvasively monitor tissue oxygen tension (FIG. 8) using subcutaneous implants. Changes in oxygen tension ($pO_2$) within subcutaneously-implanted devices were monitored 7 days and 28 days after implantation. Note how the oxygen tension at the implant site ranges between 20-40 mm Hg (Day 7) when the recipient animal is breathing room air. However, by 4 weeks post-transplantation (Day 28) the tissue $pO_2$ is substantially higher (60-70 mm Hg). Rodent $SpO_2$ (dotted lines) was measured using a rodent $SpO_2$ monitor.

Example 4: Tissue Preservation with MNBs

Figure 9:
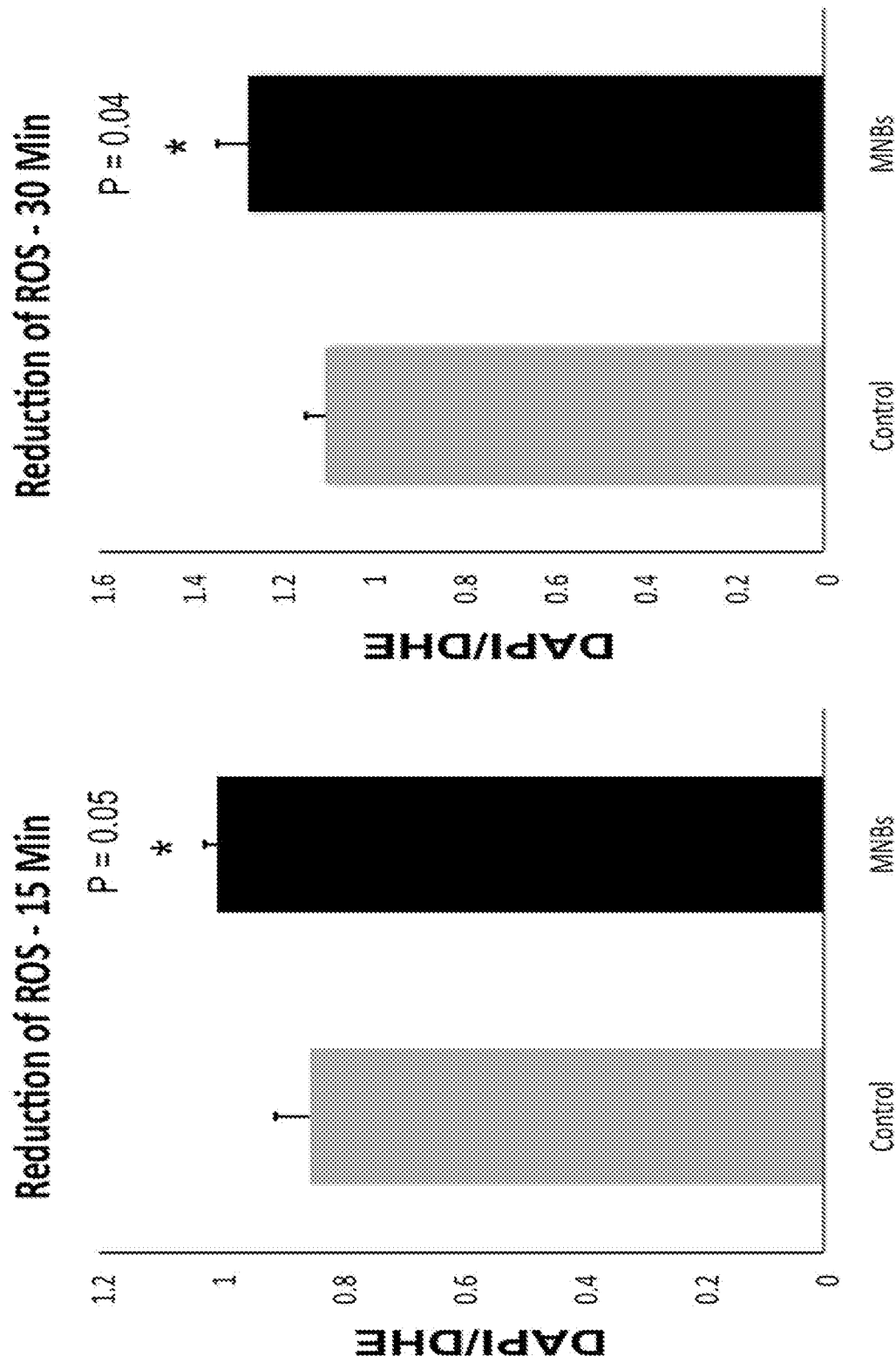
FIG. 9 is a plot showing ROS levels in MNB-treated lipoaspirate compared to lipoaspirate treated with buffer alone. After each incubation, the samples were snap frozen and sectioned for fluorescent staining. Each sample was stained with dihydroethidium (DHE) and 4',6-diamidino-2-phenylindole (DAPI) to assess ROS and positive nuclear staining, respectively. The sections were imaged, and the fluorescence was quantified to determine the DAPI/DHE ratio.
Figure 10:
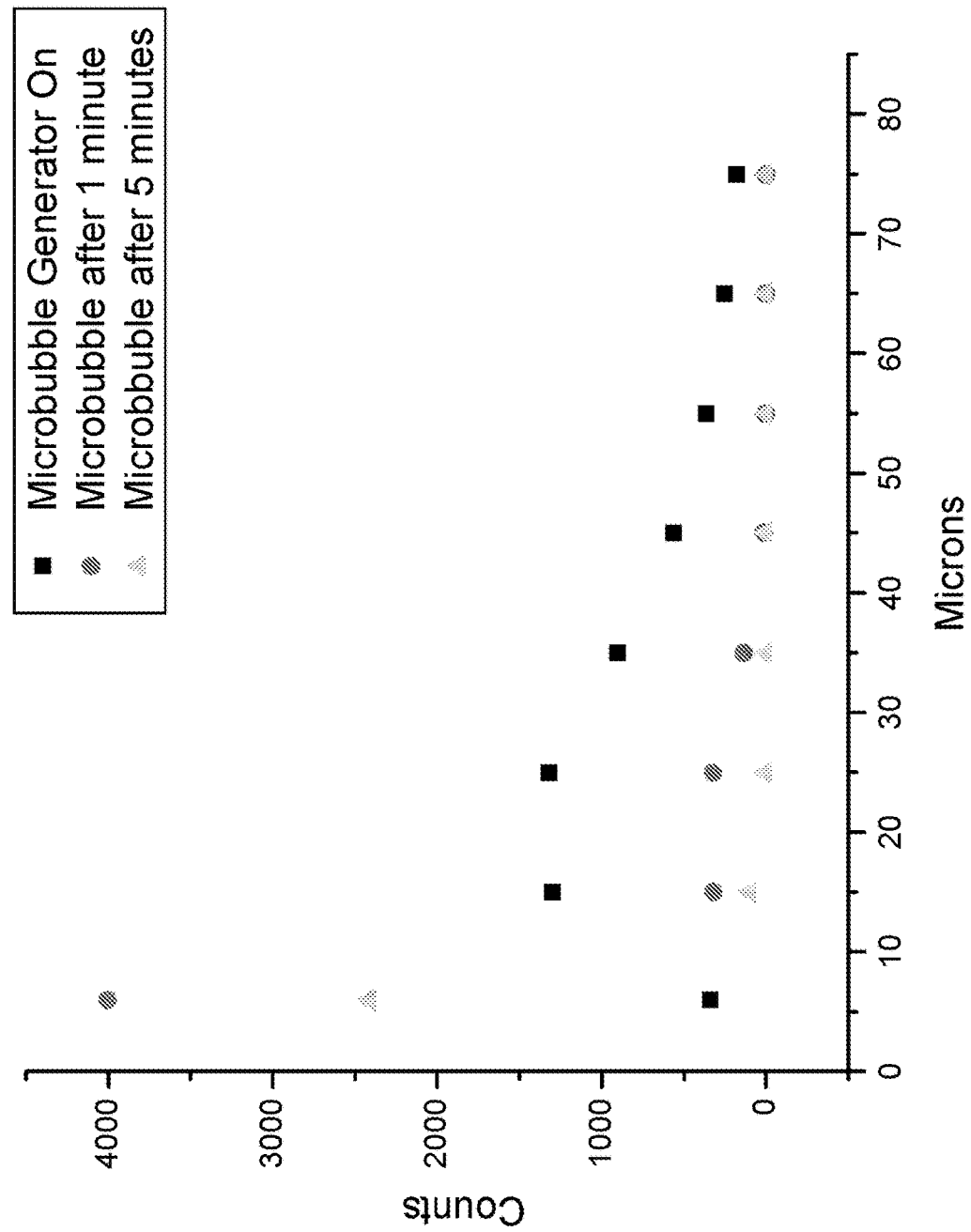
FIG. 10 is a plot of microbubble size during and after generation.

To demonstrate tissue preservation using the MNB solution, human lipoaspirate from a routine liposuction case was maintained at room temperature for 24 hours. The oxygenated MNBs were infused into phosphate buffered saline (PBS) at a concentration >20 mg/L using our custom MNB generator. The lipoaspirate was bathed in either PBS or PBS+MNBs for 15, 30 or 60 minutes on a rocker. At each time point, the samples were snap frozen in liquid nitrogen, cut to a thickness of 25 μm and stained with dihydroethidium (DHE) and 4',6-diamidino-2-phenylindole (DAPI). The images were obtained using a fluorescence microscope. Positive nuclear staining (DAPI) versus reactive oxygen species (ROS) staining (DHE) were quantified and are represented as a ratio (DAPI/DHE). The standard lipoaspirate that was bathed in oxygenated MNBs expressed a significant reduction in accumulated ROS at 15 and 30 minutes when compared to the control group (1.01±0.04 vs 0.85±0.13, p=0.05 and 1.27±0.22 vs. 1.10±0.14, p=0.05 respectively) (FIG. 9). There was no comparable reduction in ROS for either group at 1 hour (data not shown).

Example 5: Negative Pressure Wound Therapy with MNB Instillation

The use of MNB oxygenated solutions for instillation combined with NPWT should significantly aid in the healing of soft tissue injuries especially when the healing process is impaired due to diabetes.

Twelve adult female YMP are infused with 150 mg/kg body weight (bw) of the beta cell toxin STZ (Sigma) via a central venous catheter over 10 min (buffered solution: 1 g STZ in 10 mL sodium citrate buffer freshly prepared). In addition, to avoid hypoglycemia due to the insulin release by the destroyed beta cells, 200 mL of a 5% glucose solution is given over one hour after STZ application. Blood sugar readings are done on capillary blood from the ears. The first drop is discarded, and the second is placed on a test strip of the Ascensia Contour® blood glucose monitoring system (Bayer Health Care; Mishawaka, USA). Blood sugar is tested before and after STZ application. Like humans, the YMP are considered diabetic if their fasting blood glucose level is >126 mg/dL (7 mmol/L) or they have a spontaneous blood glucose level of >200 mg/dL (11.1 mmol/L). Based on previous studies, YMP become diabetic within 24 h after the application of STZ.

Two weeks after diabetes is confirmed in the 12 adult female YMP, the surgeries are performed. For the surgical procedures, the pigs are anesthetized with tiletamine plus zolazepam and xylazine and maintained during the procedures with an isoflurane inhalant anesthetic. Heart rate, blood pressure, body temperature, respiratory rate and tidal volume are monitored during the procedures. A pair of round, 5 cm diameter dorsal excisional wounds is surgically created on either side of the spine using a scalpel, with removal of the full thickness of the tissue down to the muscle fascia (including the epidermis, dermis and the subdermal and subcutaneous fat layers). Light pressure is applied to stop the bleeding, and the wounds are gently wiped clean with a saline moistened gauze.

One wound on each animal receives saline irrigation and the other the MNB solution. Pre-sterilized dressings are pre-cut into disks 5 cm in diameter by 1.5 cm thick. The therapy parameters are summarized in Table 1.

TABLE 1

Therapy Protocol

| Therapy | Instillation solution | Negative Pressure | Instillation Cycles | Soak time |
|---|---|---|---|---|
| NPWT - saline | saline | −125 mmHg | Every 3 hrs (approx. 8 cycles/day) | 10 mins |
| NPWT - MNB | MNB | −125 mmHg | Every 3 hrs (approx. 8 cycles/day) | 10 mins |

Following the manufacturer's instructions for use, the wound with the dressing is covered with a V.A.C.® Drape, two small holes are made in the drape, and a T.R.A.C.™ Pad and an instillation pad are applied to each hole. The T.R.A.C.™ Pad and the instillation pad are connected to a prototype V.A.C.ULTA™ Therapy System and programmed to deliver continuous negative pressure therapy at −125 mmHg, and sterile normal saline or MNB solution is instilled every 3 hours (approximately 8 times daily) with a 10-minute soak time. The dressings are changed every 3 days post-surgery until day 18 (i.e. at days 3, 6, 9, 12, and 15 and 18), and the animals are euthanized after 7, 10, 14 and 18 days of therapy.

Duragesic (fentanyl transdermal system) patches are placed on the pinna to alleviate pain in response to wounding. Polyurethane film dressings, circumferential Elastoplast and piglet harnesses with conduits allow the piglets to roam and the inlet+outlet tubes to be connected to devices outside of the enclosure.

At day 0, after the wound creation, all of the wounds are photographed under standardized conditions using a digital camera (IXY Digital 90; Canon, Tokyo, Japan) and the area determined using image analysis software (ImageJ). This assessment procedure is repeated during each treatment/dressing change session (at days 3, 6, 9, 12, 15 and 18). Each measurement is compared to day 0 and is recorded as a percentage of the original. After the images are obtained, the measurements are made by an observer who is blinded to which treatment the animal received. The complete epithelialization time is also recorded.

$pO_2$ is determined using OSM as described previously. The OSM impregnated alginate beads is injected into the subcutaneous tissue surrounding the wound. The pig does not have a mobile panniculus carnosus, and healing by skin contracture and mobility of the skin layer is not pronounced. Thus, the subcutaneous placement of the beads is possible without migration of these beads. The same methods of oxygen monitoring are employed: every 3 days (days 3, 6, 9, 12, 15 and 18), the dressings are removed and the tissue oxygenation levels are measured in the surrounding tissues. New dressings are then applied or the animal is euthanized if applicable (at days 7, 10, 14, and 18).

Example 6: MNB Solution Generation for Hydrosurgery

The benefits of micro-nanobubble application to wound sites to improve debris removal and improve local tissue oxygenation have been demonstrated (Klopfer, Micro and Nanobubbles for Wound Healing Applications: University of California, Irvine; 2015). Extending upon this work, a delivery system has been developed that provides a high-pressure micro-nanobubble (MNB) solution via a spray jet nozzle (FIG. 1 and FIG. 2). The spray jet nozzle itself is a commercially available patient-interface consumable for the Smith and Nephew Versa Jet II Hydrosurgery system. In our demonstration design, we have constructed a high pressure feed system that generates micro-nanobubble solution and subsequently removes waste solution from the wound site. The micro-nanobubble solution is generated via a pressurization—expansion type generator. A pre-generation system supplies an air-water mix under pressure to pressurization chamber via an expansion nozzle. After releasing, a crude MNB solution is created. This pre-generation step combines a shear/turbine-type generator, implemented here with a gear pump, with a pressurization—expansion type generator, to bypass the turbulent flow and/or agitation constraints required for efficient MNB generation in a pressurization—expansion type generator. The effect is rapid MNB generation without physical agitation at low generation flow rates. After pressurization of NMB solution, expansion occurs through a generation nozzle with final output directed toward the application wand.

Example 7: MNB Analysis and Wound Oxygenation

Figure 11:
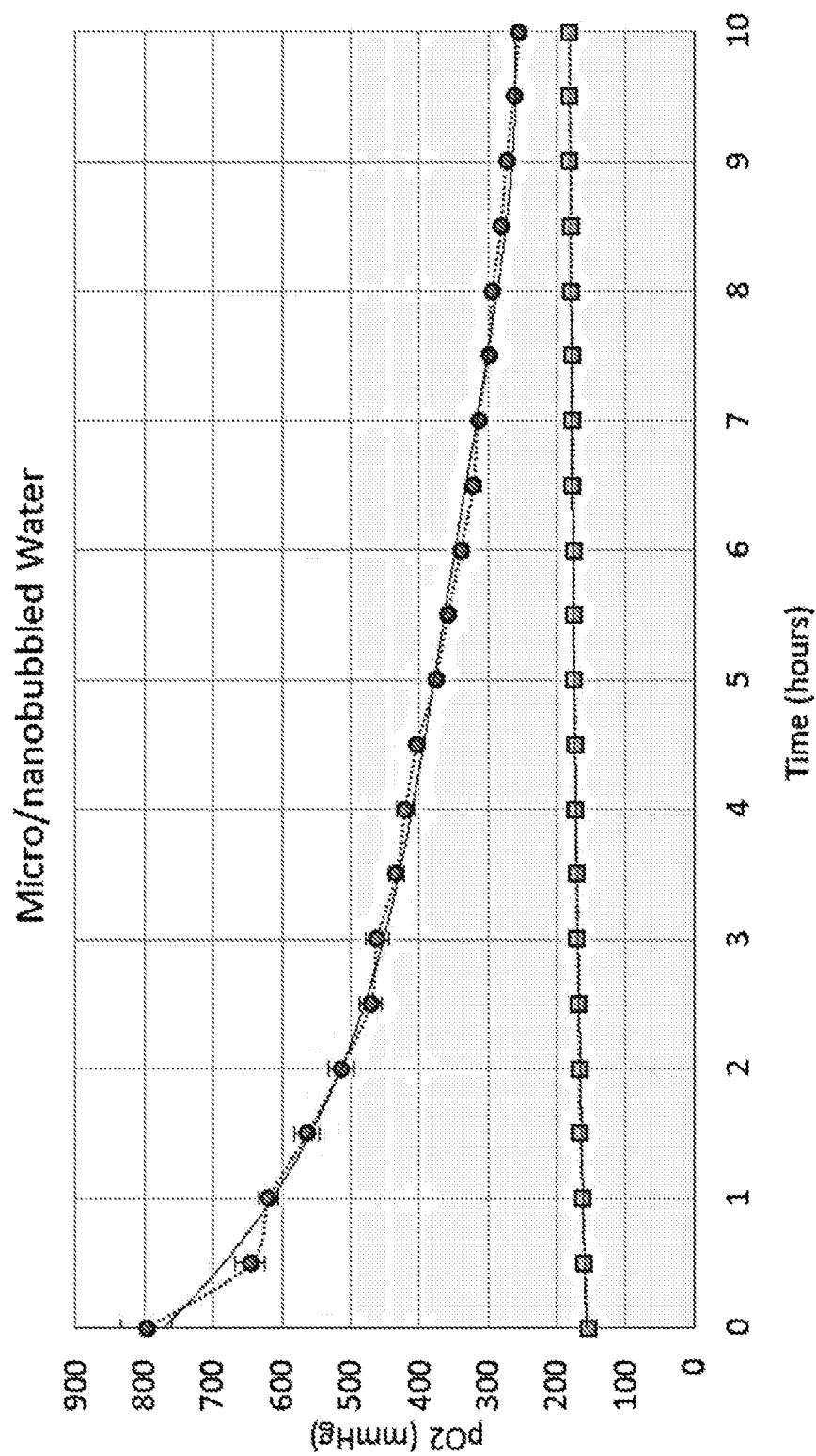
FIG. 11 is a plot of the oxygen carrying capacity of micro-nanobubble-infused water (circles) vs untreated water (squares) over a 10-hour period at room temperature 26° C. (n=4).
Figure 12:
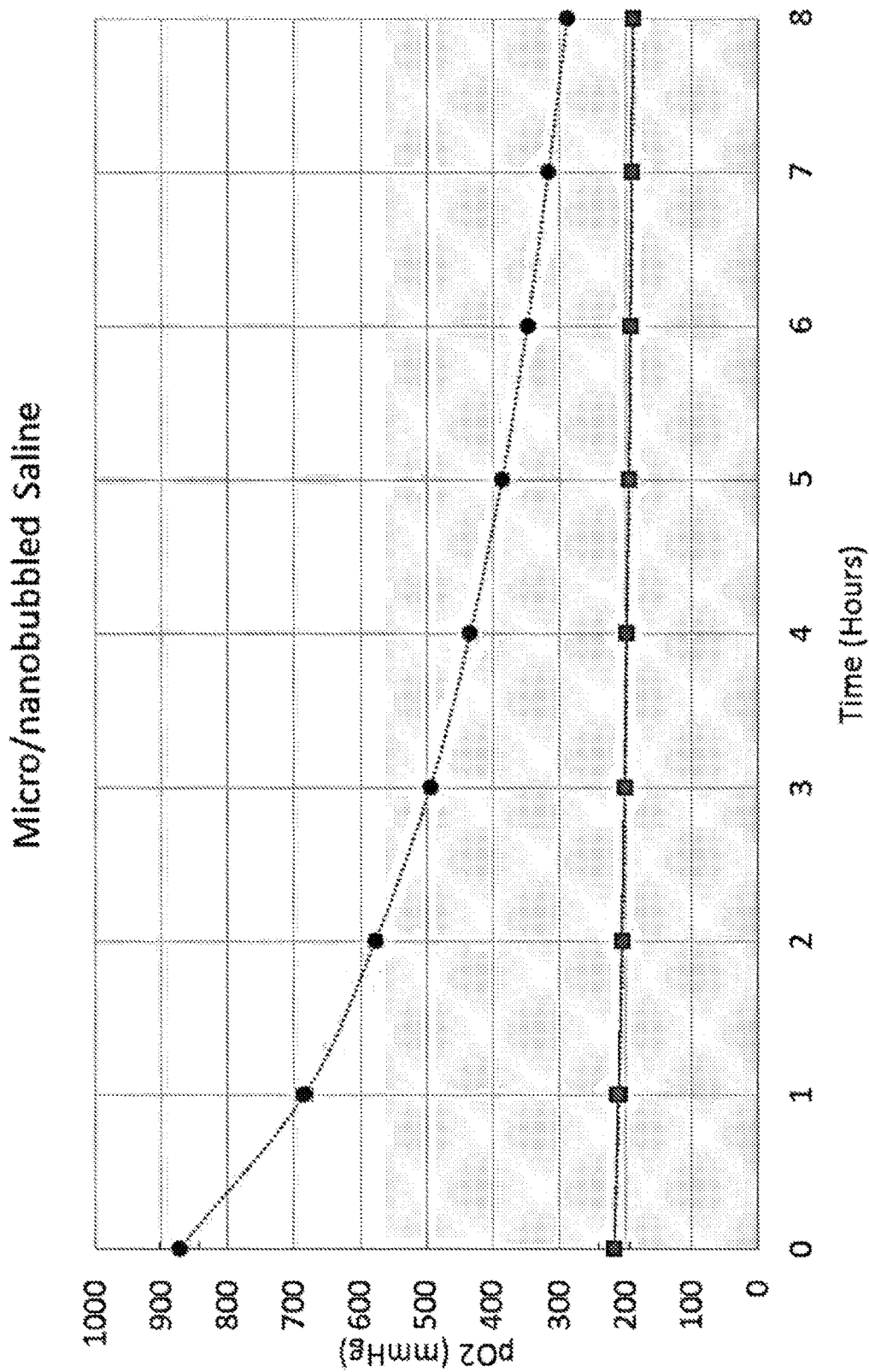
FIG. 12 is a plot of the oxygen carrying capacity of micro-nanobubble-infused saline (circles) vs untreated saline (squares) over an 8-hour period at room temperature 26° C. (n=3).
Figure 13:
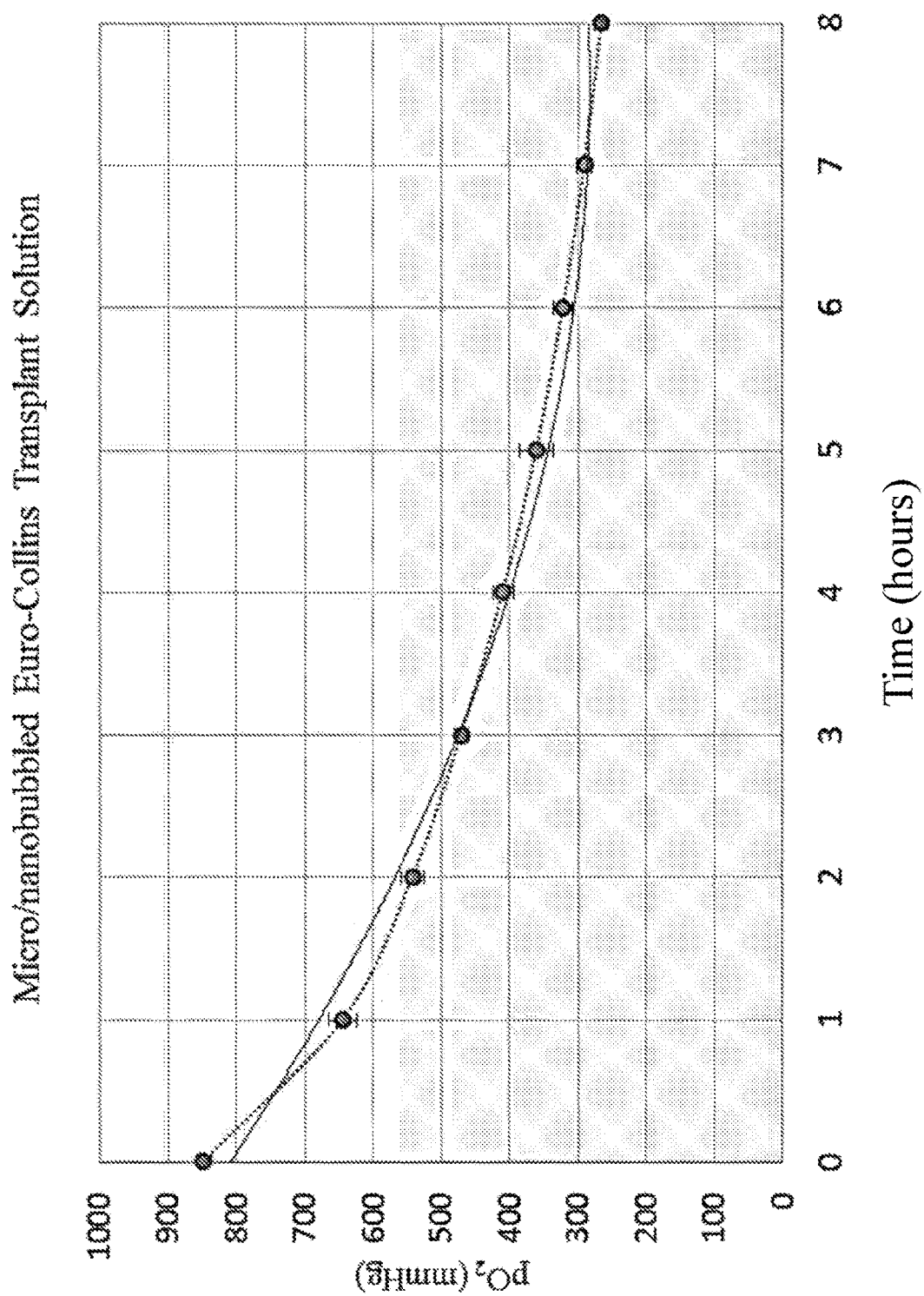
FIG. 13 is a plot of the oxygen carrying capacity of a Micro-nanobubble-infused Euro-Collins Transplant solution over an 8-hour period at room temperature 26° C. (n=1).
Figure 14:
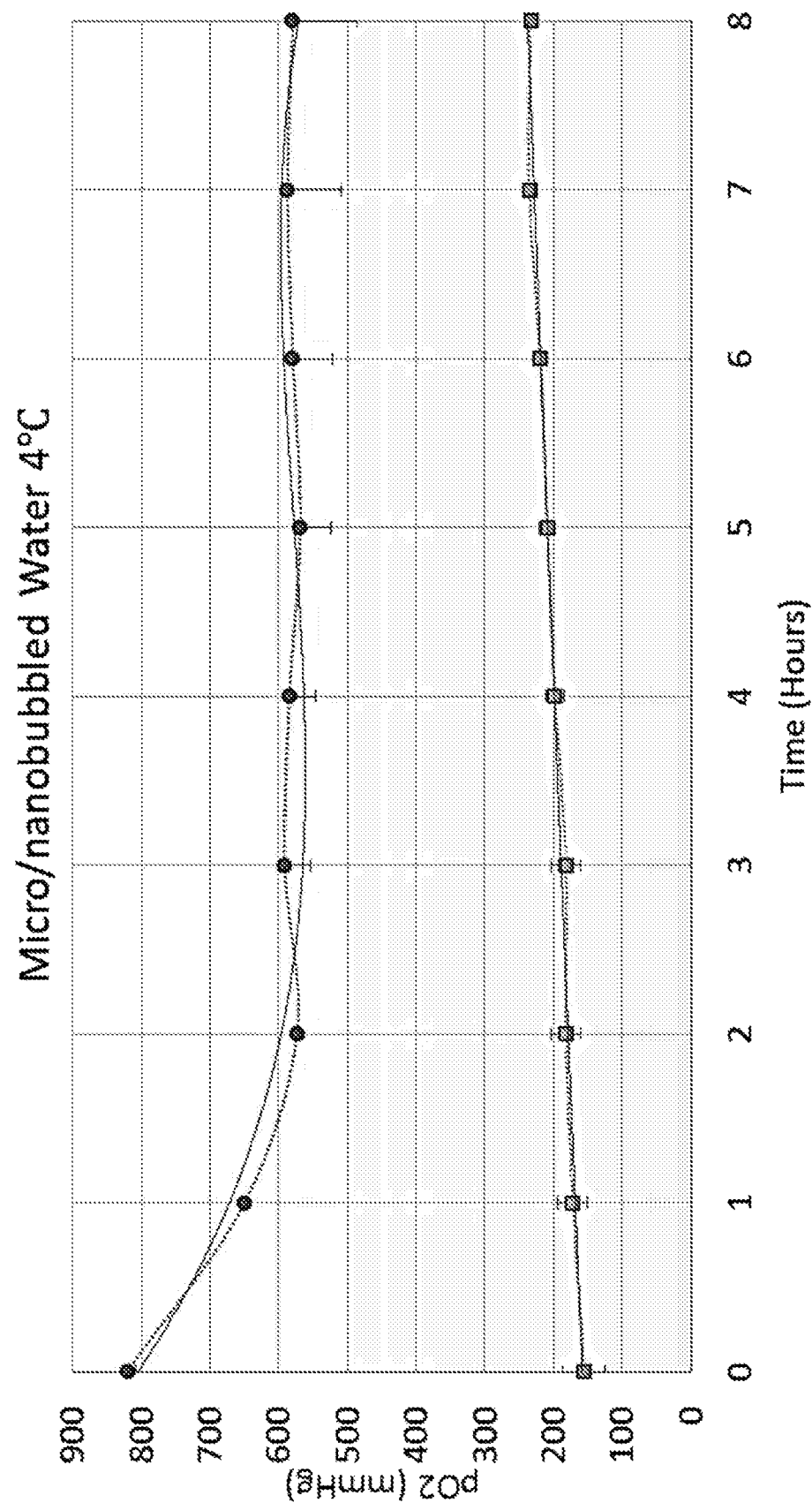
FIG. 14 is a plot of the oxygen carrying capacity of micro-nanobubble-infused water (circles) vs untreated water (squares) over 8-hour period at 4° C. (n=2).
Figure 15:
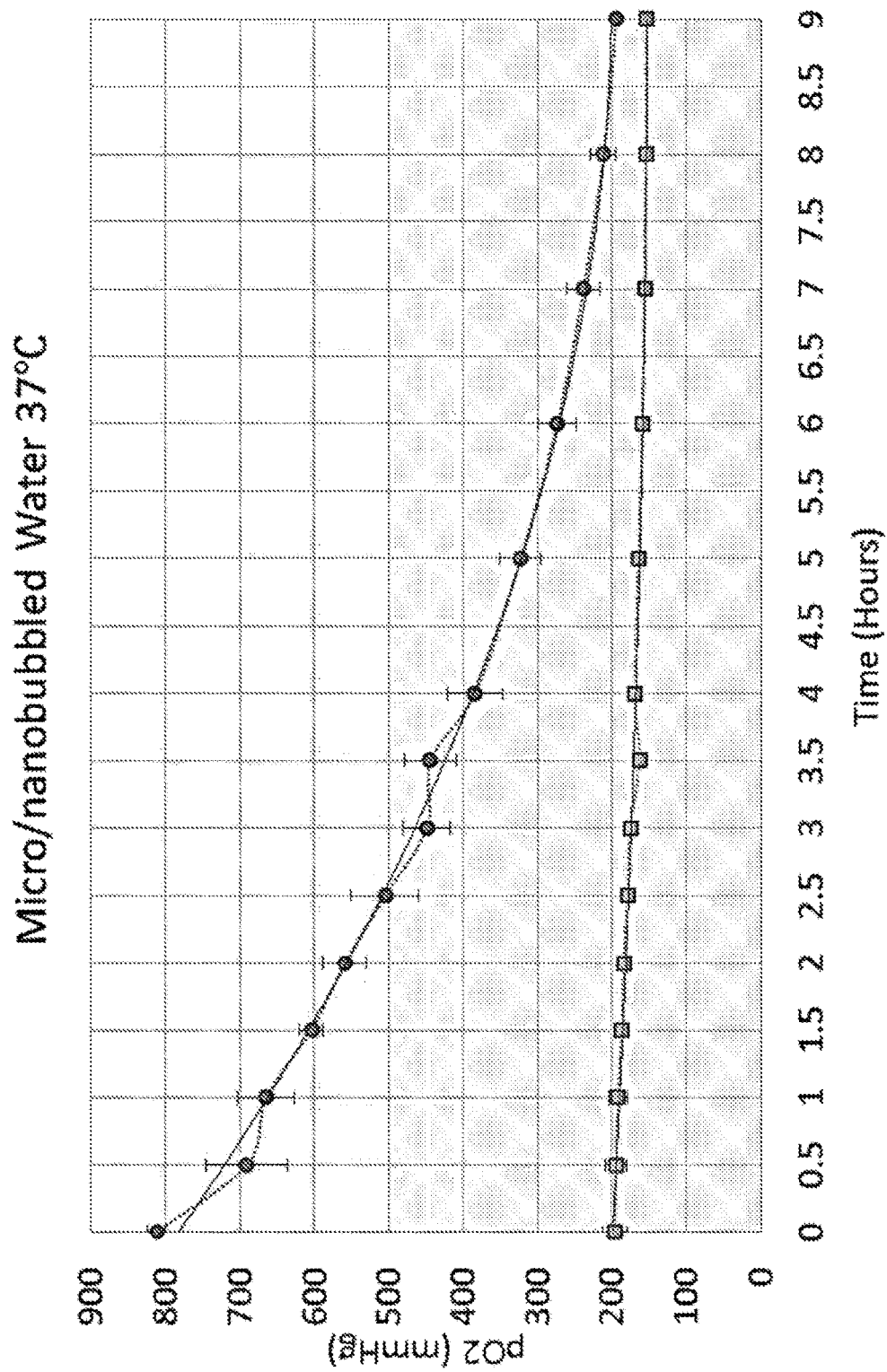
FIG. 15 is a plot of the oxygen carrying capacity of micro-nanobubble-infused water (circles) vs untreated water (squares) over 9-hour period at 37° C. (n=3).
Figure 16:
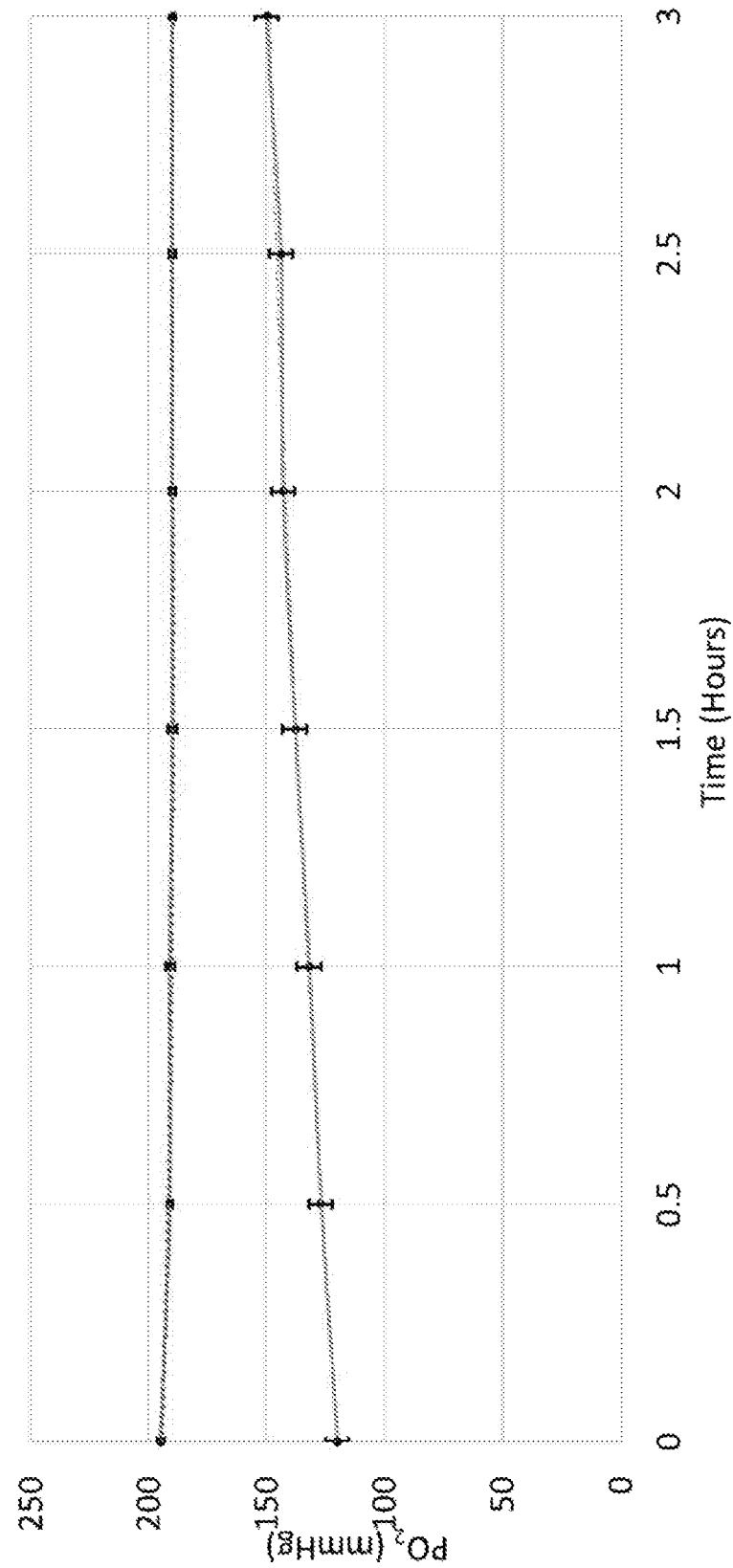
FIG. 16 is a plot of the air carrying capacity of micro-nanobubble-infused water (blue) vs untreated water (orange) over a 3 hour period at 26° C. (n=3).
Figure 17:
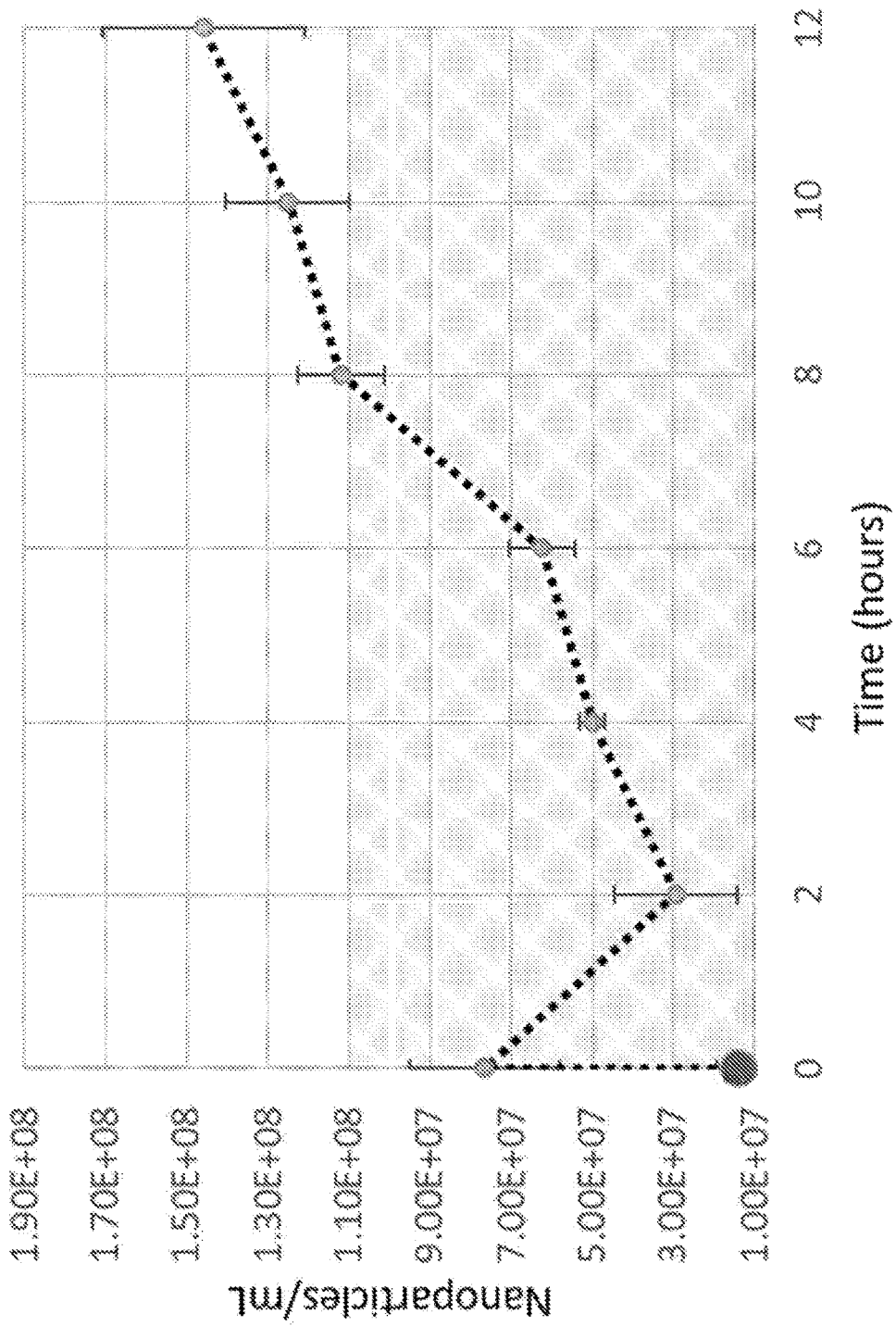
FIG. 17 is a plot of micro-nanobubble concentration over a 12 hour period using NanoSight particle counter and size, which shows increased micro-nanobubble levels with time reaching $1.58 \times 10^8$ mL at time 12 hours. This is consistent with the theory that microbubbles shrink with time to produce more nanobubbles.
Figure 18:
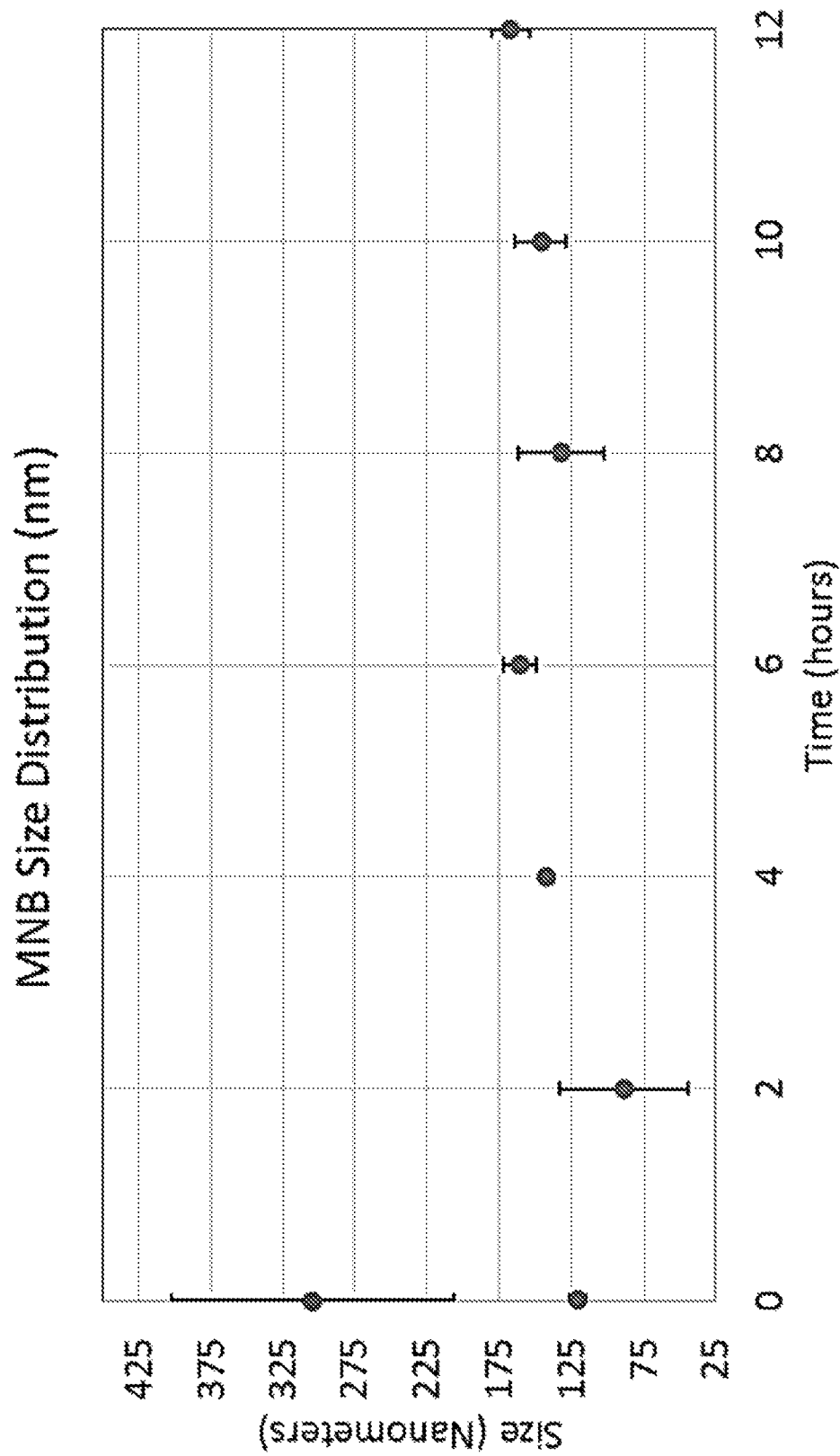
FIG. 18 is a plot of micro-nanobubble size distribution using a NanoSight particle counter and sizer, which shows the presence of nanobubbles with an average size of 125-175 nm over all time points (blue). The red data point at 304.5 nm is the average particulate size in untreated lab water.

Given the significant gap in research on MNBs for wound and transplantation tissue oxygenation, resources have been allocated to investigate the use of MNBs for these purposes. The MNBs were generated using a portable and inexpensive gear pump modified to produce large quantities of MNBs. The data presented herein bridges significant gaps in the literature regarding bubble oxygen carrying capacity. Presented is a quantification of the oxygen carrying capacity and time course of MNBs produced in a variety of different solutions (FIGS. 11, 12, & 13). Initial $pO_2$ levels as high as 800 mmHg (7.5× Control) can be achieved, and high oxygen levels can be sustained for more than 10 hours. In addition, examination of temperature effects at 4° C. and 37° C. on the stability of MNBs have shown that low temperature improves oxygen carrying capacity, while higher temperatures reduce oxygen levels at all time points (FIG. 14 and FIG. 15). Importantly, the method of recording oxygen levels in solution employed herein has been validated using an adaptation of an automated blood gas analyzing device (ABL 800 Flex Radiometer Medical Aps, Copenhagen, Denmark) by comparing these recordings to a standard chemical technique for ascertaining oxygen levels, the Winkler titration. FIG. 16 shows the air carrying capacity of micro-nanobubble-infused water compared to untreated water at 26° C. Particle count and sizing analysis using laser particle counting techniques (FIG. 17 and FIG. 18) (Nano-Sight, Amesbury, United Kingdom) have confirmed the presence of MNBs in solution. The MNBs have an average size of 120 nm, persist for more than 12 hours and are present in concentrations up to 108 per-milliliter (FIG. 18).

Significant preliminary data have shown the positive survival benefits of MNBs on pancreatic islet cells prior to transplantation. Islet cells harvested and preserved in MNB solution prior to transplantation have higher cell survival compared to those in control media (Table 2).

TABLE 2

Pancreatic Islet Oxygenation

| Solution Type | Islet # (t: 0) | # Survived (t: 48 hour) | % Viability (t: 48 hours) |
|---|---|---|---|
| CMRL (control) | 1000 islets | 534 islets | 96.1% |
| CMRL + MNB ($O_2$): | 1000 islets | 768 islets | 95.2% |

1000 Islets were cultured to either CMRL (control: $pO_2$ = 112 mmHg) or CMRL + MNB ($O_2$) $pO_2$ = 795 mmHg. At 48 hours islets were counted for cell survival and percent viability. CMRL refers to Connaught Medical Research Laboratories solution, an islet cell culturing solution.

Figure 19:
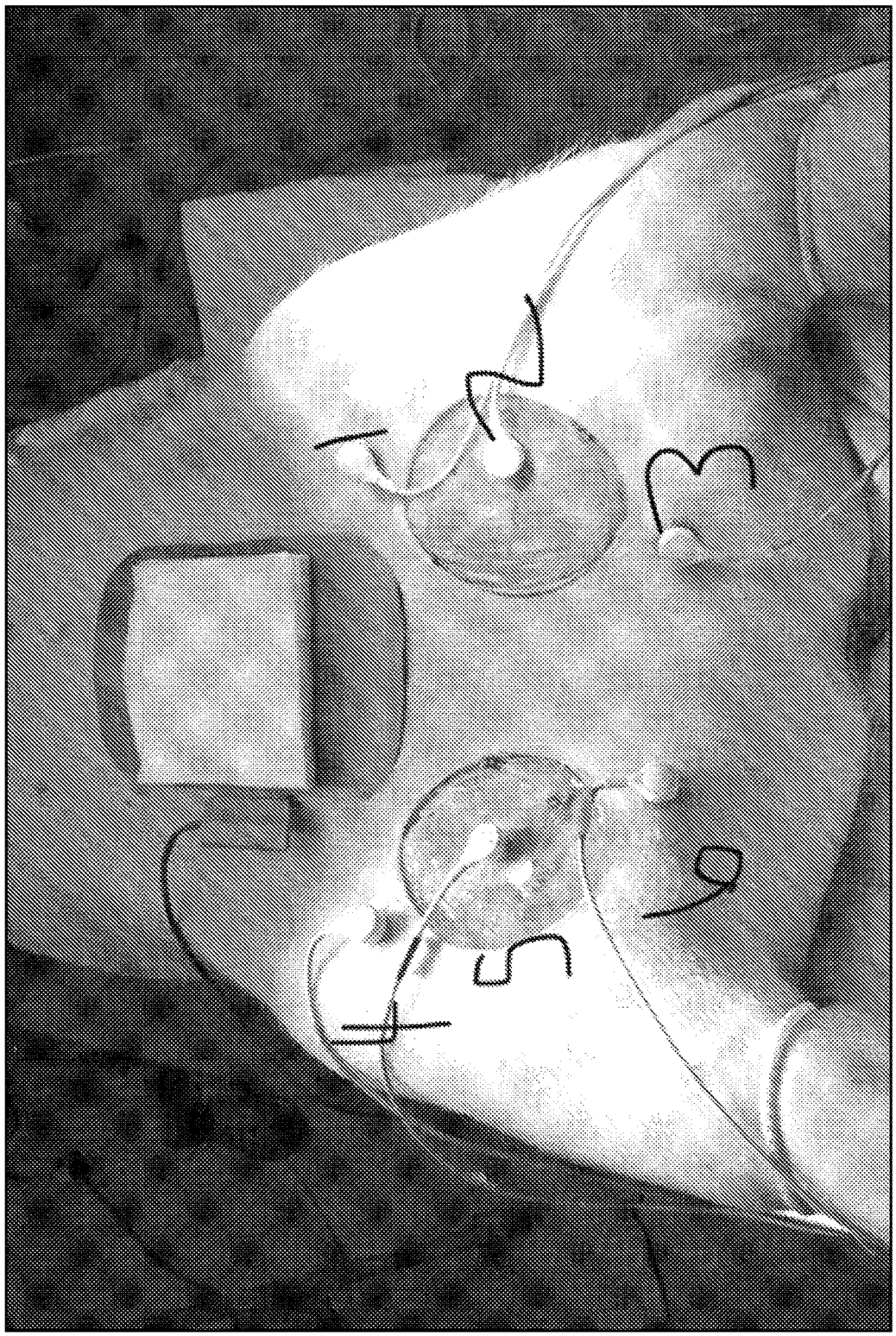
FIG. 19 is a photograph demonstrating experiment setup for porcine wound oxygenation. Two 3-inch porcine wounds were created in a euthanized pig and subjected to either MNB saline or saline. $TcpO_2$ levels were recorded using a Radiometer TCM4 $TcpO_2$ meter.

The pilot data also indicate that MNBs improve tissue oxygenation. When micro-nanobubbled saline solutions are used to irrigate porcine wounds, improvements are observed in transcutaneous tissue oxygenation (from 86 to 167 mmHg) versus the controls (from 15 to 38 mmHg) (Table 3 & FIG. 19).

TABLE 3

MNB Porcine Wound Oxygenation

| | Saline | Saline + MNB ($O_2$) |
|---|---|---|
| Wound 1 ($TcpO_2$) | 38 mmHg | 86 mmHg |
| Wound 2 ($TcpO_2$) | 15 mmHg | 167 mmHg |

3-inch diameter porcine wounds were irrigated for 3 minutes with either Saline or Saline with MNB ($O_2$) and $TcpO_2$ measurements were taken using Radiometer TCM4 (Radiometer, Medical Aps, Copenhagen Denmark). The saline solution had a $pO_2$ = 126 mmHg and the Saline + MNB ($O_2$) solution had a $pO_2$ = 681 mmHg prior to application on the wound.

These results corroborate established evidence that micro-nanobubbles carry high levels of oxygen. Particle counting has demonstrated the number and size of the particles, and pilot studies have shown that MNBs confer greater cell survival for harvested pancreatic islet cells prior to transplantation.

Example 8: Pancreas Islet Cell Oxygenation

Figure 20:
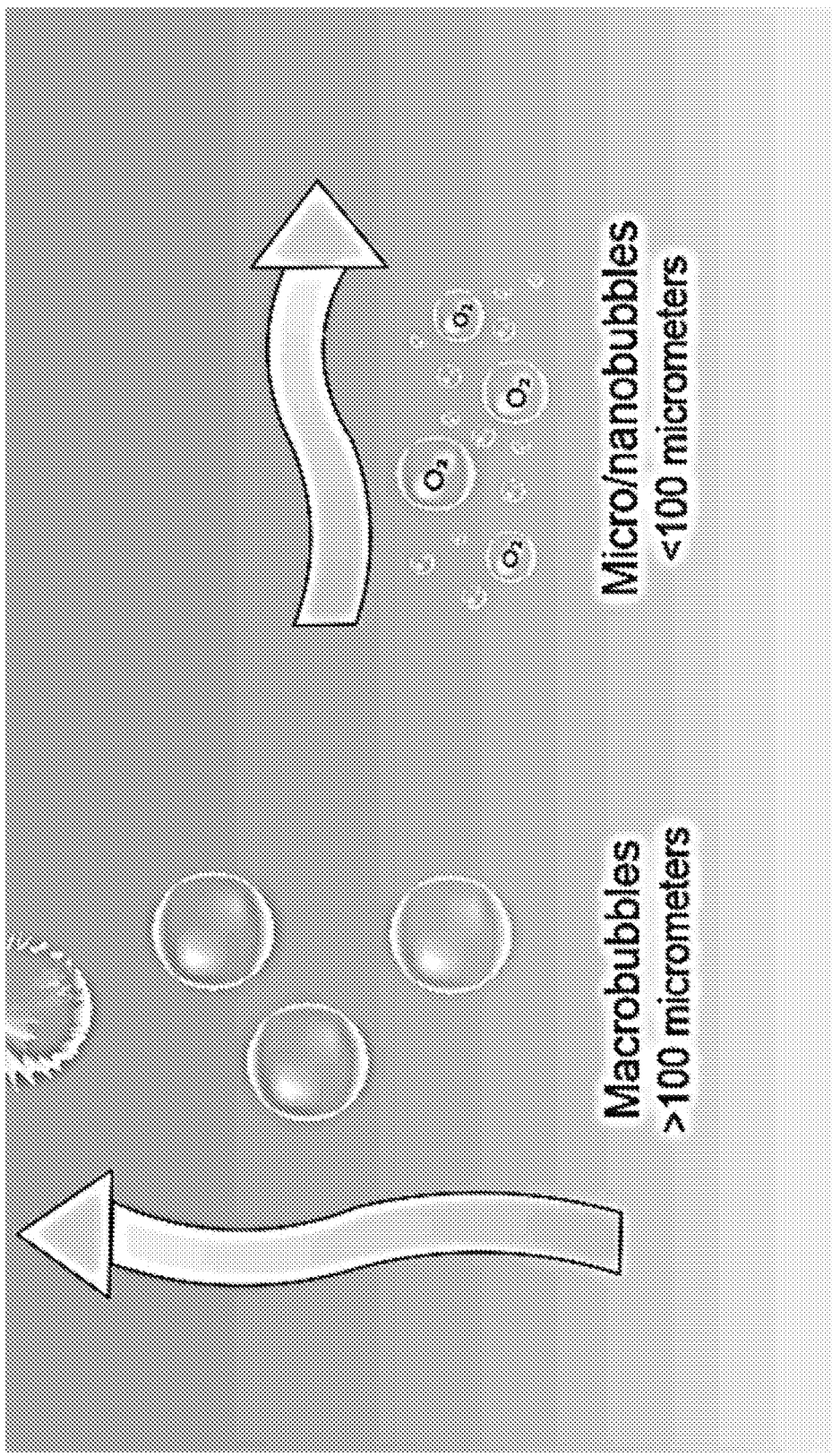
FIG. 20 is an illustration depicting the differing behavior of regular bubbles and micro-nanobubbles in a liquid environment.

The survival and preservation of transplanted tissue (kidney, heart, fat grafts) are directly tied to and limited by ischemia time. Micro-nanobubbles (MNBs) are miniature gaseous voids that allow for improved oxygenation of a tissue (FIG. 20). Given their high oxygen carrying capacity, MNBs offer an inexpensive technology for oxygenating transplantable tissue and improving cell survival and viability. A priority in the field of islet cell transplantation for Type 1 Diabetes is to preserve every single islet count due to the shortage of donors and consistent low recovery of islets with current isolation procedures (Barshes, et al., J Leukoc Biol. 2005; 77(5):587-597; Ricordi and Strom, *Nat Rev Immunol.* 2004; 4(4):259-268). Islet cell survival and viability can be improved when immersed in MNBs, and these results can be generalized to other autologous and allogenic transplants.

Figure 21:
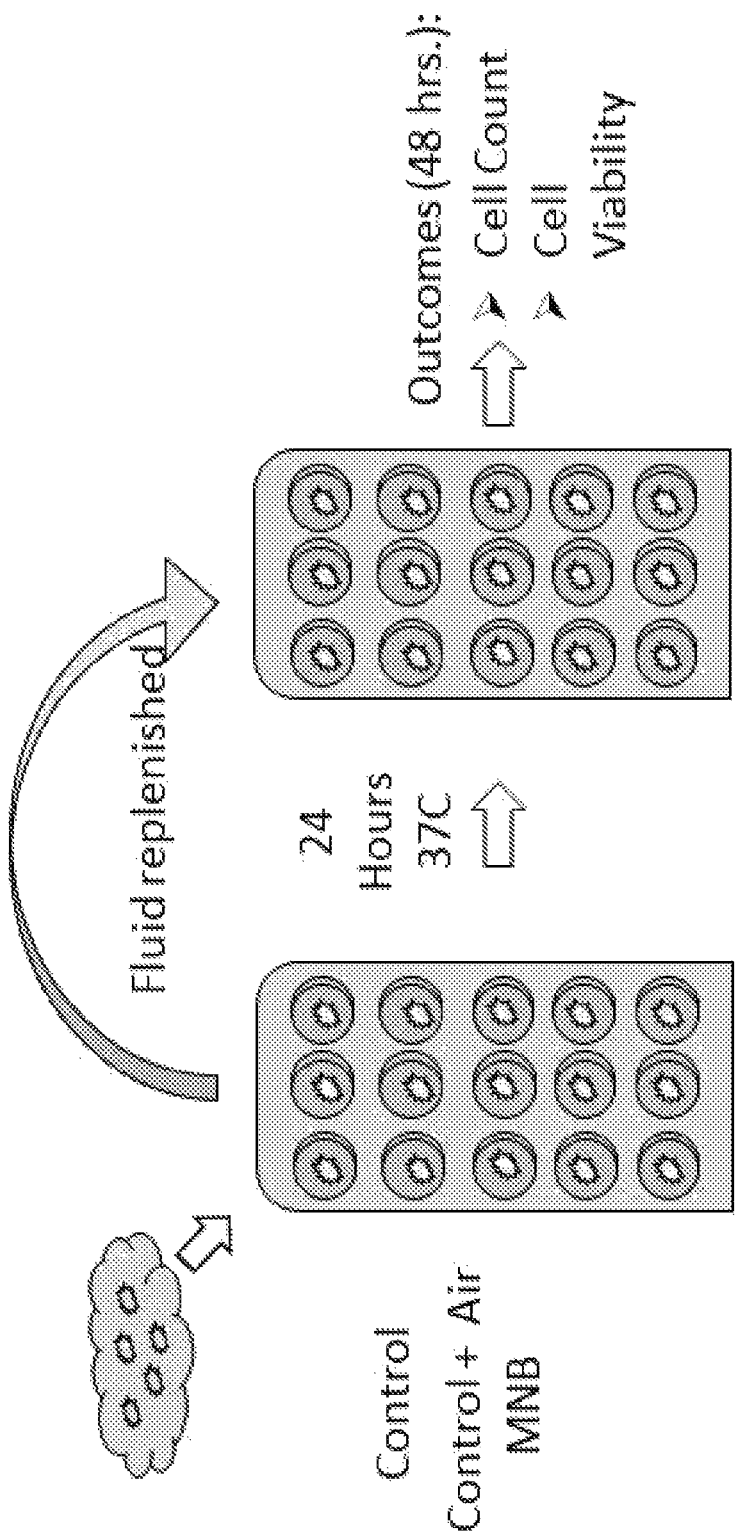
FIG. 21 is an illustration depicting an exemplary method for the oxygenation of pancreatic islet cells.

The general methodology of this study is illustrated in FIG. 21. Rat pancreatic islet cells were harvested and split into 3 groups starting with 500 cells in each group—these were cultured in JPI media overnight. On day 0, media was changed to either control media ($pO_2$: 210 mmHg); control media with dissolved air ($pO_2$: 210 mmHg) or micro-nanobubbled solution ($pO_2$: 223 mmHg). Media was replenished under the same conditions at 24 hours. On day 2, the number of living islet cells were counted using dithizone staining and their viability was assessed using the calceinAM/propidium assay. All experiments were replicated 5 times. The results of this study are presented in Table 4 and FIG. 22.

TABLE 4

Islet Cell Oxygenation

| Solution Type | Islet number (t: 0) | # Survived (t: 48 hrs.) | % Viability (t: 48 hrs.) |
|---|---|---|---|
| Control | 500 Islets | 104 Islets | 87 ± 1% |
| Control + Air | 500 Islets | 92 Islets | 87 ± 1% |
| MNB | 500 Islets | 223 Islets | 96 ± 1% |

Harvested Islet cells preserved in MNB solution had a significant improvement in cell survival and viability when compared to the controls. MNBs improve Islet survival by 114% (223 cells vs. 104 cells p<0.05) and viability by 10% (96% vs. 87% p<0.05).

MNBs added to standard media significantly improve oxygenation and survival of harvested pancreatic islet cells prior to transplantation compared to control media. These findings are very encouraging in the field of islet cell transplantation for Type 1 diabetes given the demonstrated increase in preservation of robust cells. MNBs may also improve oxygenation and survival of a variety of other tissues including fat grafts, chronic wounds and large organs.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. An apparatus for administration of micro-nanobubbles to a tissue, comprising:
    in a first flowpath, a liquid source, a gas source downstream of the liquid source, a micro-nanobubble generation pump downstream of the gas source, and a decompression nozzle downstream of the micro-nanobubble generation pump;
    in a second flowpath, an air pump;
    wherein the first flowpath connects with the second flowpath downstream of the air pump and downstream of the decompression nozzle; and
    a treatment applicator downstream of the decompression nozzle and the air pump;
    wherein the treatment applicator is connected to a vacuum pump and configured to deliver a micro-nanobubble liquid solution and therapeutic negative pressure to a tissue site.

2. The apparatus of claim 1, further comprising:
    a pressurization chamber downstream of the decompression nozzle and the air pump, and upstream of the treatment applicator.

3. The apparatus of claim 2, further comprising:
    at least one pressure sensor downstream of the pressurization chamber and upstream of the treatment applicator.

4. The apparatus of claim 1, further comprising
a collection chamber between the vacuum pump and the treatment applicator.

5. The apparatus of claim 1, further comprising:
at least one pressure sensor downstream of the air pump and upstream of the treatment applicator.

6. The apparatus of claim 1, wherein the treatment applicator is a hydrosurgery system application wand.

7. The apparatus of claim 1, wherein the treatment applicator is a dressing selected from the group consisting of: air tight dressings, air-permeable dressings, occlusive dressings, and saturated dressings.

8. The apparatus of claim 1, wherein the treatment applicator is a vessel with an inlet and an outlet.

9. The apparatus of claim 1, wherein the gas source is an oxygen tank.

10. The apparatus of claim 1, wherein the gas source is an ozone generator.

11. The apparatus of claim 1, wherein the gas source is ambient air.

12. A kit for the treatment of a tissue with a solution of micro-nanobubbles, the kit comprising an apparatus of claim 1 and an instructional material.

* * * * *